United States Patent [19]
Abatjoglou et al.

[11] Patent Number: 4,731,486
[45] Date of Patent: Mar. 15, 1988

[54] HYDROFORMYLATION USING LOW VOLATILE PHOSPHINE LIGANDS

[75] Inventors: Anthony G. Abatjoglou, Charlestown; David R. Bryant, So. Charleston, both of W. Va.

[73] Assignee: Union Carbide Corporation, Danbury, Conn.

[21] Appl. No.: 932,002

[22] Filed: Nov. 18, 1986

[51] Int. Cl.$^4$ .............................................. C07C 45/50
[52] U.S. Cl. .................................... 568/454; 568/451
[58] Field of Search ................................ 568/451, 454

[56] References Cited

U.S. PATENT DOCUMENTS

| Re. 31,812 | 1/1985 | Kuntz | 568/454 |
|---|---|---|---|
| 3,527,809 | 9/1970 | Pruett et al. | 260/604 |
| 3,959,385 | 5/1976 | Juergen et al. | 260/604 HF |
| 3,968,136 | 7/1976 | Walker et al. | 260/449 L |
| 4,148,830 | 4/1979 | Pruett et al. | 568/454 |
| 4,151,209 | 4/1979 | Paul et al. | 260/604 HF |
| 4,158,020 | 6/1979 | Stautzenberger et al. | 260/604 HF |
| 4,159,999 | 7/1979 | Stautzenberger et al. | 260/604 HF |
| 4,162,261 | 7/1979 | Kaplan | 260/449 L |
| 4,211,719 | 7/1980 | Walker et al. | 260/449 L |
| 4,247,486 | 1/1981 | Brewester et al. | 568/454 |
| 4,248,802 | 2/1981 | Kuntz | 568/454 |
| 4,283,562 | 8/1981 | Billig et al. | 568/454 |
| 4,302,547 | 11/1981 | Hart | 518/701 |
| 4,306,084 | 12/1981 | Pettit | 568/451 |
| 4,329,511 | 5/1982 | Hackman et al. | 568/454 |
| 4,399,312 | 8/1983 | Russell et al. | 568/454 |
| 4,400,548 | 8/1983 | Abatjoglou et al. | 568/454 |
| 4,453,022 | 6/1984 | McCain et al. | 568/618 |
| 4,480,138 | 10/1984 | Hackman et al. | 568/454 |
| 4,483,801 | 11/1984 | Sabot | 260/505 |
| 4,483,802 | 11/1984 | Gartner et al. | 260/505 |
| 4,504,588 | 3/1985 | Gartner et al. | 502/24 |
| 4,510,332 | 4/1985 | Matsumoto et al. | 568/454 |
| 4,523,036 | 6/1985 | Cornils et al. | 568/454 |
| 4,533,755 | 8/1985 | Cornils | 568/454 |
| 4,578,523 | 3/1986 | Bahrmann | 568/454 |
| 4,593,126 | 1/1986 | Cornils et al. | 568/454 |
| 4,633,021 | 12/1986 | Hanes | 568/454 |

FOREIGN PATENT DOCUMENTS

| 0103810 | 5/1984 | European Pat. Off. |  |
|---|---|---|---|
| 0133410 | 6/1984 | European Pat. Off. |  |
| 0144745 | 11/1984 | European Pat. Off. |  |
| 0147824 | 12/1984 | European Pat. Off. |  |
| 0157316 | 3/1985 | European Pat. Off. |  |
| 0158246 | 3/1985 | European Pat. Off. |  |
| 0158572 | 3/1985 | European Pat. Off. |  |
| 0160249 | 4/1985 | European Pat. Off. |  |
| 0163234 | 5/1985 | European Pat. Off. |  |
| 0163233 | 5/1985 | European Pat. Off. |  |
| 0216315 | 4/1987 | European Pat. Off. |  |
| 2627354 | 12/1976 | Fed. Rep. of Germany | 568/454 |
| 3347406 | 7/1983 | Fed. Rep. of Germany |  |
| 3411034 | 9/1984 | Fed. Rep. of Germany |  |
| 2478078 | 9/1981 | France |  |
| 83-05374 | 9/1983 | Spain |  |
| 1350822 | 4/1974 | United Kingdom |  |
| 2085874 | 5/1982 | United Kingdom | 568/454 |

OTHER PUBLICATIONS

Kirk-Othmer, "Encyclopedia of Chemical Technology" 3rd ed., vol. 22, pp. 338-339, 364-367 (1983).
Kirk-Othmer, "Encyclopedia of Chemical Technology" 3rd ed., vol. 18, p. 634 (1982).
Snyder & Kirkland, "Introduction to Modern Liquid Chromatography" (1974) pp. 215-218.
Hildebrand & Scott, "The Solubility of Non-Electrolytes" (1964) pp. 424-434.
"J. Chem. Soc." (1958) pp. 276-288.
Suss-Fink et al., "J. of Molecular Catalysis", vol. 16, (1982) pp. 231-242.
U.S. Application Ser. No. 884,197–filed Jul. 10, 1986.

Primary Examiner—Werren B. Lone
Attorney, Agent, or Firm—R. J. Finnegan

[57] ABSTRACT

A nonaqueous hydroformylation process for producing aldehydes using low volatile, organic solubilized monosulfonated tertiary phosphine metal salt ligands.

45 Claims, No Drawings

HYDROFORMYLATION USING LOW VOLATILE PHOSPHINE LIGANDS

TECHNICAL FIELD

This invention relates to transition metal-phosphorus complex catalyzed hydroformylation using monosulfonated tertiary phosphine metal salt ligands. More particularly this invention relates to the rhodium-monosulfonated tertiary phosphine metal salt ligand complex catalyzed non-aqueous hydroformylation of olefinic compounds to their corresponding aldehydes.

BACKGROUND OF THE ART

The hydroformylation of an olefinic compound with carbon monoxide and hydrogen to produce aldehydes using an organic solubilized transition metal-phosphorus ligand complex catalyst is well known in the art.

It is further well known that the phosphorus ligand employed in such catalyzed hydroformylation processes may have a direct effect on the success of such a given process. Moreover, the selection of the particular phosphorus ligand to be used in any such transition metal catalyzed hydroformylation process depends in the main on the end result desired, since the best overall processing efficiency may require a compromise between numerous factors involved. For example, in hydroformylation such factors as aldehyde product selectivity (i.e., normal to branched chain aldehyde product ratios), catalyst reactivity and stability, and ligand stability are often of major concern in the selection of the desired phosphorus ligand to be employed. For instance, U.S. Pat. No. 3,527,809 teaches how alpha olefins can be selectively hydroformylated with rhodium-triorganophosphine or triorganophosphite ligand complexes to produce oxygenated products rich in normal aldehydes, while U.S. Pat. Nos. 4,148,830 and 4,247,486 disclose both liquid and gas cycle operations directed to the same result using a rhodium triarylphosphine ligand complex catalyst. U.S. Pat. No. 4,283,562 discloses that branched-alkylphenylphosphine or cycloalkylphenylphosphine ligands can be employed in a rhodium catalyzed hydroformylation process in order to provide a more stable catalyst against intrinsic deactivation. U.S. Pat. No. 4,400,548 discloses that bisphosphine monoxide ligands can be employed to provide rhodium complex catalysts of improved thermal stability useful for the hydroformylation production of aldehydes.

However, despite the obvious benefits attendant with the prior art references mentioned above, the search continues for phosphorus ligands which will more effectively satisfy additional ligand requirements, particularly with regard to ligand volatility.

For example, rhodium complex catalyzed hydroformylation processes are preferably carried out in a non-aqueous hydroformylation reaction medium containing an olefinically unsaturated compound, aldehyde product, and both the solublized catalyst complex and free excess phosphorus ligand, i.e., ligand not tied to or bound to the rhodium complex. In such processes the desired aldehyde product is preferably separated and recovered from the reaction product medium by distillation, and in the case of continuous liquid catalyst recycle operations, the non-volatilized catalyst-ligand containing residue is recycled to the reactor. Accordingly, an important requirement of such processes is the effective separation and recovery of the desired aldehyde product from its hydroformylation reaction product medium without excessive phosphorus ligand and/or catalyst complex loss. Thus in such non-aqueous hydroformylation processes, and in particular liquid catalyst recycle processes, the volatility of the phosphorus ligand is also of primary concern, since continuous removal (stripping) of the phosphorus ligand during aldehyde product separation via distillation can result not only in high phosphorus ligand loss which must be replaced, but can also lead to changes in the catalyst properties and even eventual catalyst deactivation. Indeed, if the rate of such simultaneous volatilization of the phosphorus ligand is too high an additional ligand recovery/recycle scheme may be required in order for the process to be economical.

While, this problem of ligand volatility and aldehyde product separation in non-aqueous hydroformylation may not be as overwhelming when low molecular weight olefins, such as propylene, are hydroformylated using conventional tertiary phosphines such as triphenylphosphine, it is still of some concern and said problem increases and magnifies when the process is directed to the hydroformylation of long chain olefinic compounds (e.g., $C_6$ to $C_{20}$ olefins) to produce their corresponding higher molecular weight aldehydes due to the high temperatures necessary to volatilize such high molecular weight aldehyde products from the hydroformylation reaction product medium. Likewise ligand loss due to volatility, when higher boiling aldehyde condensation by-products, such as trimers, etc. are desired to be removed e.g., from catalyst containing hydroformylation residues, in order to recover the catalyst and ligand, is also of major concern to the art regardless of whether or not such aldehyde condensation by-products are the result of hydroformylating low (e.g., $C_2$–$C_5$) or high (e.g., $C_6$–$C_{20}$) molecular weight olefins.

It has been proposed to use aqueous solutions of sulfonated aryl phosphine compounds as the phosphorus ligand, such as the sulfonated triphenylphosphine salts disclosed e.g., in EPC No. 163234 and U.S. Pat. Nos. 4,248,802, 4,399,312 and the like, as the phosphorus ligand in the hydroformylation process to facilitate the separation and recovery of the rhodium complex catalyst. However, all such prior art methods also involve the employment of an two-phase liquid, non-homogenous hydroformylation reaction medium made up of both an organic phase containing the reaction starting materials and/or products and an aqueous or water phase containing the catalyst complex and sulfonated phosphine ligands. Moreover, such aqueous or water phase type hydroformylation systems in general require high reactor pressures and/or high rhodium concentrations to overcome intrinsically low hydroformylation reaction rates and may also require buffers or phase transfer reagents and/or the use of larger and more costly processing apparatus equipment.

Therefore there is a definite need in the hydroformylation art for low volatile phosphorus ligands which will function effectively in a non-aqueous rhodium catalyzed hydroformylation process with regard to hydroformylating both low molecular weight olefins (e.g., $C_2$ to $C_5$ olefins) and in particular long chain, high molecular weight olefinic compounds, (e.g., $C_6$ to $C_{20}$ olefins).

DISCLOSURE OF THE INVENTION

It has now been discovered that monosulfonated tertiary phosphine metal salt ligands may be employed as the phosphorus ligand in non-aqueous Group VIII transition metal-phosphorus complex catalyzed hydroformylation processes to provide numerous advantages.

For instance, while the monosulfonated tertiary phosphine metal salt ligands employable herein are water-soluble, they are generally insoluble or very poorly soluble in most aldehydes and/or olefins and in particular high molecular weight non-polar aldehydes and/or olefins and thus are not readily suitable as the candidates for phosphorous ligand in rhodium catalyzed non-aqueous, hydroformylation processes. However, it has now been discovered that the monosulfonated tertiary phosphine metal salt ligands employable herein can be rendered readily soluble in rhodium catalyzed non-aqueous hydroformylation reaction mediums by the use of certain added organic solubilizing agents and/or mixtures thereof and thus can be readily employable as the phosphorous ligand in such non-aqueous type rhodium catalyzed processes. Further, it has been discovered that certain monosulfonated tertiary phosphine metal salts in certain instances may be inherently sufficiently soluble in some non-aqueous hydroformylation reaction mediums as to be directly employable as the phosphorous ligand in such non-aqueous type rhodium catalyzed hydroformylation processes.

The extremely low volatility of the monosulfonated tertiary phosphine salt ligands employable herein is very beneficial to the subject hydroformylation art. For example, due to such low volatility, separation of the aldehyde product from the rhodium complex catalyst containing reaction product medium can be easily accomplished by vaporization (distillation) even when the non-aqueous hydroformylation process is directed to producing high molecular weight aldehyde products, such as those derived from the hydroformylation of long chain olefins of $C_6$ to $C_{20}$ carbon atoms without undue ligand and/or catalyst loss. Moreover, the monosulfonated tertiary phosphine metal salt ligands employable herein can help promote the rhodium catalyzed hydroformylation of both low ($C_2$ to $C_5$) and high to $C_{20}$) molecular weight olefins at highly acceptable catalyst activity rates even at conventional low hydroformylation pressures (e.g., less than 500 psig.) and/or with low rhodium concentrations without unduly sacrificing processing efficiency and/or catalyst stability. Furthermore, the monosulfonated tertiary phosphine metal salt ligands employable herein have not been observed to unduly, adversely promote aldehyde by-product heavies formation. Moreover, the non-aqueous hydroformylation process of this invention involving the hydroformylation of high molecular weight olefins can be readily retrofitted to existing non-aqueous hydroformylation design apparatus and equipment conventionally employed to hydroformylate low molecular weight olefins, without the need for major modifications of same.

Another unexpected advantage of the monosulfonated tertiary phosphine metal salt ligands employable in this invention is that the straight (normal) chain to branched (iso) chain aldehyde product ratio (selectivity) of the hydroformylation process may be varied by simply varying the metal cation group of such ligands, in addition to being able to vary said aldehyde product ratio by adjusting carbon monoxide partial pressure and/or phosphine ligand concentration. Such normal to iso (N/I) selectivity control is of significant importance in hydroformylation in as much as it allows one to target the yield of whichever particular aldehyde product ratio is desired. Moreover, such control in being able to vary the N/I aldehyde product ratios may be achieved herein without unduly adversely effecting the process efficiency and/or catalyst stability of the process.

Thus it is an object of this invention to provide an improved rhodium catalyzed hydroformylation process wherein said process is carried out in a non-aqueous hydroformylation reaction medium using low volatile monosulfonated tertiary phosphine metal salt ligands. Other objects and advantages of this invention will become readily apparent from the following written description and appended claims.

Accordingly, a generic aspect of this invention can be described as an improved non-aqueous hydroformylation process for producing aldehydes which comprises reacting an olefinically unsaturated organic compound with carbon monoxide and hydrogen, in a non-aqueous hydroformylation reaction medium containing the olefinically unsaturated organic compound, aldehyde product, solubilized Group VIII transition metal-phosphorus ligand complex catalyst and solubilized free phosphorus ligand, the improvement comprising employing as the phosphorus ligand of said complex catalyst and as said free phosphorus ligand, a monosulfonated tertiary phosphine metal salt having the general formula

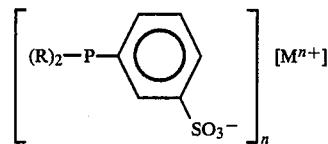

wherein each R group individually represents a radical containing from 1 to 30 carbon atoms selected from the class consisting of alkyl, aryl, alkaryl, aralkyl and cycloalkyl radicals, wherein M represents a metal cation selected from the group consisting of alkali and alkaline earth metals, and wherein n has a value of 1 or 2 corresponding to the valance of the particular metal cation represented by M, and wherein said hydroformylation reaction medium also contains at least a sufficient amount of an added organic solubilizing agent capable of rendering the Group VIII transition metal-monosulfonated tertiary phosphine metal salt ligand complex catalyst and free monosulfonated tertiary phosphine metal salt ligand employed, soluble in said hydroformylation reaction medium; and wherein said organic solubilizing agent is selected from the group consisting of an alkylene oxide oligomer having an average molecular weight of at least 150, an organic nonionic surfactant mono-ol having an average molecular weight of at least 300, a polar organic compound having a molecular weight of less than 150 and having a Hildebrand solubility value of at least 10, and mixtures thereof; provided that when present in the hydroformylation reaction medium, the amount of said alkylene oxide oligomer is not greater than about 35 weight percent of said medium, the amount of said organic nonionic surfactant mono-ol is not greater than about 60 weight percent of said medium, and the amount of said polar organic compound is not greater than about 6 weight percent of said medium; with the additional proviso that the total amount of added organic solubilizing agent present in said medium is not greater than about 60 weight percent of said medium.

DETAILED DESCRIPTION

Accordingly, the subject invention encompasses the carrying out of any known non-aqueous hydroformylation process for producing aldehydes by reacting an olefinically unsaturated compound with carbon monoxide and hydrogen in a non-aqueous hydroformylation reaction medium containing the olefinically unsaturated compound, aldehyde product, solubilized Group VIII transition metal-phosphorus ligand complex catalyst and solubilized free phosphorus ligand, in which both the phosphorus ligand of said catalyst and free phosphorus ligand are replaced by a monosulfonated tertiary phosphine metal salt ligand as disclosed herein. Such generic non-aqueous hydroformylation (oxo synthesis) processes are well known in the art as seen for example by U.S. Pat. Nos. 3,527,809; 4,148,830; 4,247,486 and the like. Accordingly, the reaction conditions and processing techniques of this invention may correspond if desired to any of the known reaction conditions and processing techniques heretofore employed in such conventional non-aqueous hydroformylation reactions.

For instance, the hydroformylation process can be conducted in continuous, semi-continuous, or batch fashion and involve any liquid and/or gas recycle operation, as desired. Likewise, the manner or order of addition of the reaction ingredients, catalyst, ligand, and/or added organic solubilizing agent may be accomplished in any convenient fashion desirable.

As noted, the hydroformylation reaction is carried out in a non-aqueous hydroformylation reaction medium that contains both the solubilized Group VIII transition metal-monosulfonated tertiary phosphine metal salt ligand complex catalyst and solubilized free monosulfonated tertiary phosphine metal salt ligand. By "free ligand" is meant phosphorus ligand that is not complexed with (tied to or bound to) the Group VIII transition metal atom in the active complex catalyst. Moreover, the term "non-aqueous" as employed in this invention means that the hydroformylation process of this invention is conducted, in the absence or essential absence of water, which is to say that any water, if present at all, in the hydroformylation reaction medium, is not present in an amount sufficient to cause either the process or said medium to be considered as encompassing a separate aqueous or water phase or layer in addition to an organic phase.

As noted above the monosulfonated phosphine metal salt ligands employable in this invention are those having the formula

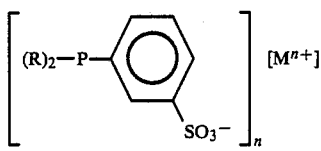

wherein each R, n and M, are the same as defined above.

Illustrative radicals represented by the R groups in the above monosulfonated tertiary phosphine salt ligand formulas include both unsubstituted and substituted monovalent hydrocarbon radicals containing from 1 to 30 carbon atoms, e.g., alkyl radicals including linear or branched, primary, secondary or tertiary alkyl radicals, such as methyl, ethyl, n-propyl, isopropyl, butyl, sec-butyl, t-butyl, t-butylethyl, t-butylpropyl, n-hexyl, amyl, sec-amyl, t-amyl, 2-ethylhexyl, n-octyl, iso-octyl, decyl, dodecyl, octadecyl, eicosyl and the like; aryl radicals such as phenyl, naphthyl, and the like; aralkyl radicals such as benzyl, phenylethyl, tri-phenylmethylethane, and the like; alkaryl radicals such as tolyl, xylyl, and the like; and alicyclic radicals such as cyclopentyl, cyclohexyl, cyclooctyl, cyclohexylethyl, and the like. Moreover, such monovalent hydrocarbon radicals may be substituted with any substituent that does not unduly adversely effect the desired results of this invention. Illustrative substituents that may be on the hydrocarbon radicals may include for example silyl radicals such as $-Si(R^9)_3$; amino radicals such as $-N(R^9)_2$; acyl radicals such as $-C(O)R^9$, acyloxy radicals such as $-OC(O)R^9$, amido radicals such as $-CON(R^9)_2$ and $-N(R^9)COR^9$, sulfonyl radicals such as $-SO_2R^9$, alkoxy radicals such as $-OR^9$; thionyl radicals such as $-SR^9$, phosphonyl radicals such as $-P(O)(R^9)_2$, as well as, halogen, nitro, cyano, trifluoromethyl, and hydroxy radicals, and the like, wherein each $R^9$ individually represents the same or different substituted or unsubstituted monovalent hydrocarbon radical having the same meaning as defined for R above, with the proviso that in amino substituents such as $-N(R^9)_2$, each $R^9$ taken together can also represent a divalent bridging group that forms a heterocyclic radical with the nitrogen atom, and in amido substituents such as $-C(O)N(R^9)_2$ and $-N(R^9)COR^9$ each $R^9$ bonded to N can also be hydrogen. Of course it is to be understood that each R group in a particular given metal salt ligand may be the same or different.

The more preferred monovalent hydrocarbon radicals represented by R are linear or branched alkyl radicals having from $C_3$ to $C_{20}$ carbon atoms, aryl radicals having from $C_6$ to $C_{12}$ carbon atoms and alicyclic radicals having from $C_5$ to $C_{12}$ carbon atoms. Preferably each R group is individually a branched chain alkyl radical having from 3 to 9 carbon atoms, phenyl or cyclohexyl radical. Most preferably the R radicals in a given monosulfonated tertiary phosphine metal salt represent a phenyl and/or cyclohexyl radical, especially phenyl.

As noted above, M in the monosulfonated tertiary phosphine metal salt ligand formula above, represents a metal cation selected from the group consisting of alkali and alkaline earth metals. Illustrative alkali metals include lithium ($Li^+$), sodium ($Na^+$), potassium ($K^+$), cesium ($Cs^+$) and rubidium ($Rb^+$), while illustrative alkaline earth metals include calcium ($Ca^{++}$), barium ($Ba^{++}$), magnesium ($Mg^{++}$) and strontium ($Sr^{++}$). Moreover as noted above by the definition of n, the metal salt ligand may contain one or two monosulfonated tertiary phosphine anion molecules corresponding to the positive valence of the metal cation M. A more preferred class of monosulfonated tertiary phosphine metal salt ligands employable herein are those wherein each R individually represents a radical selected from the group consisting of alkyl radicals containing from 3 to 20 carbon atoms (especially secondary branched chain alkyl radicals having from 3 to 9 carbon atoms such as isopropyl, t-butyl, etc.), phenyl and cyclohexyl radicals, and wherein M and n are the same as defined above.

Illustrative preferred monosulfonated tertiary phosphine metal salt ligands include e.g., those having the following general formulas:
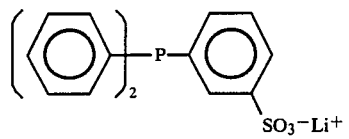
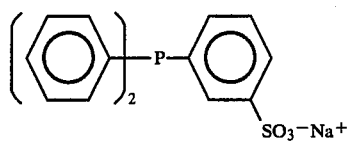
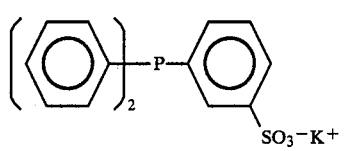
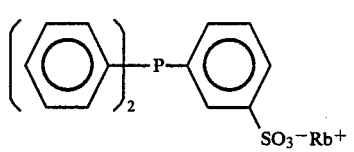
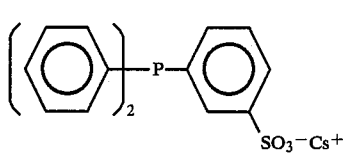
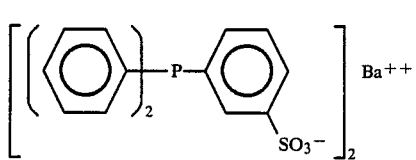
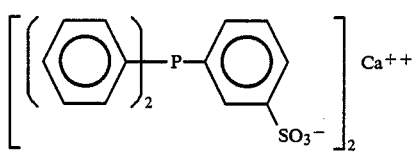
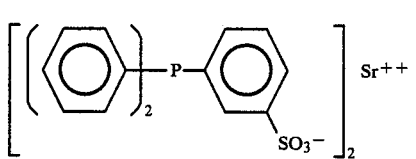
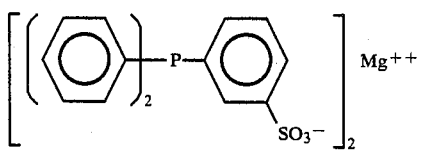
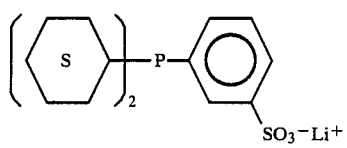
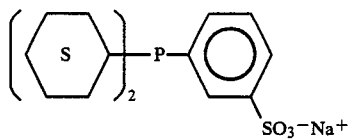
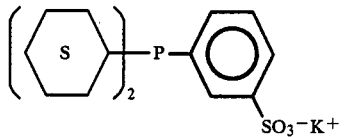
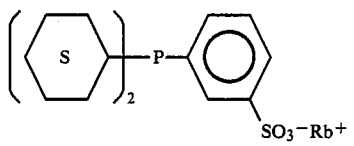
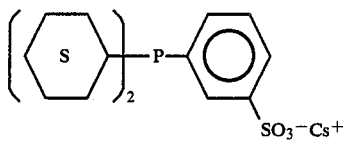
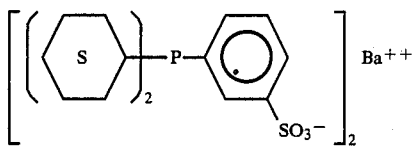
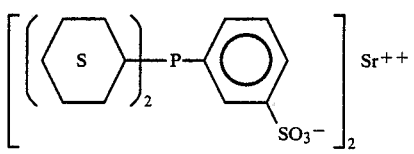
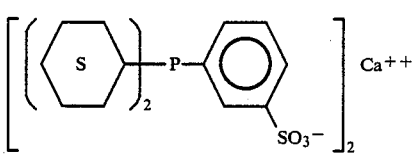
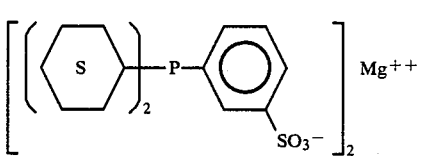
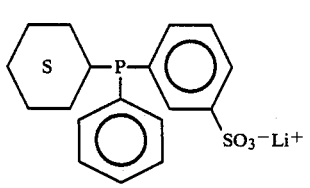

-continued
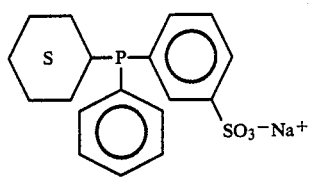
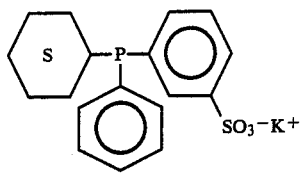
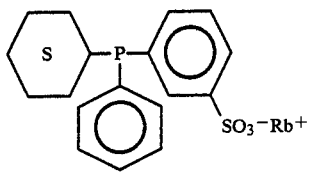
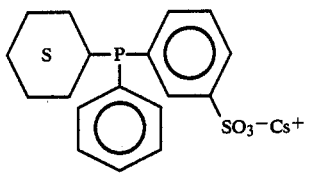
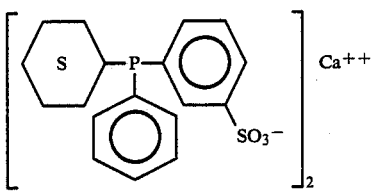
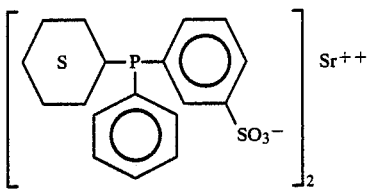
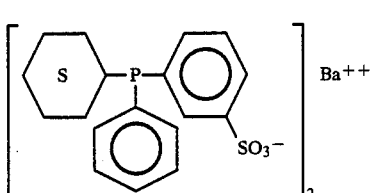
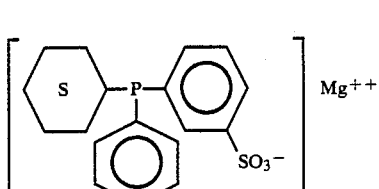
-continued
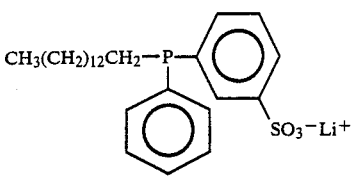
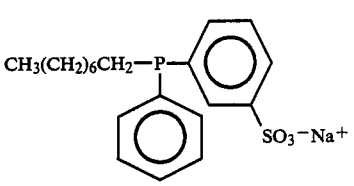
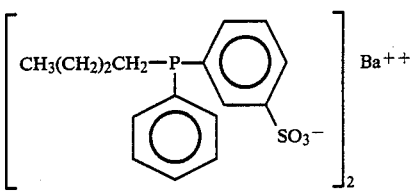
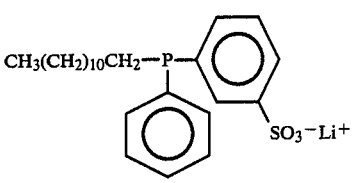
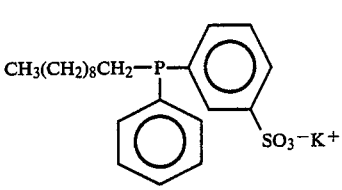
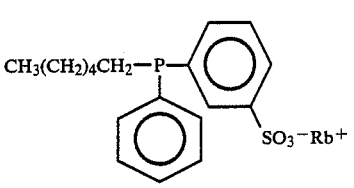
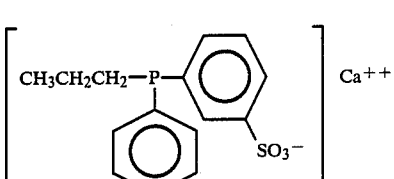
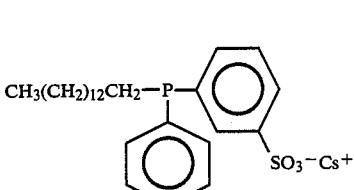

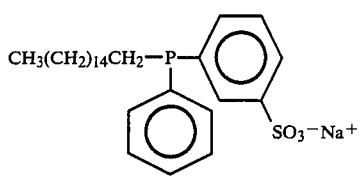
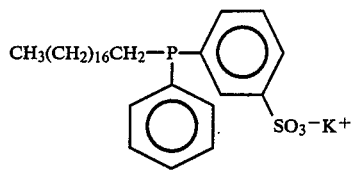
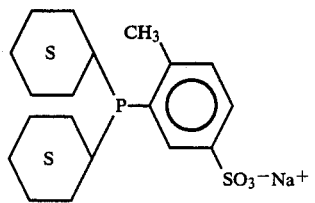
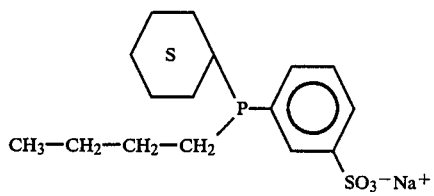
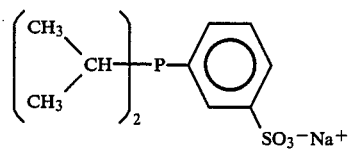
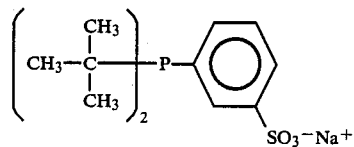
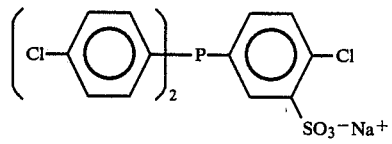
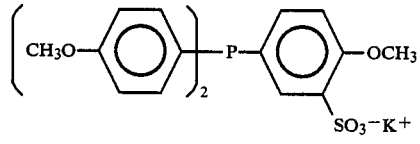
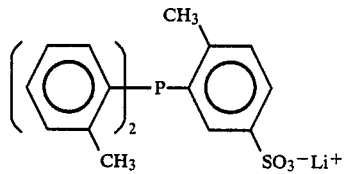
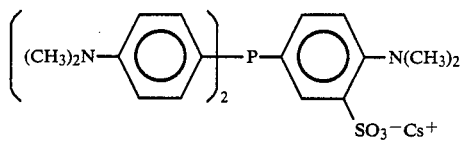
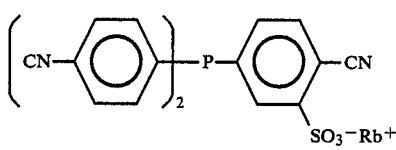
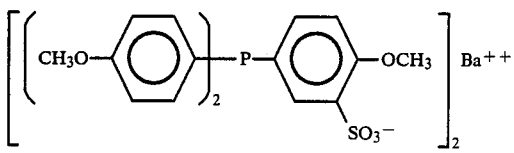
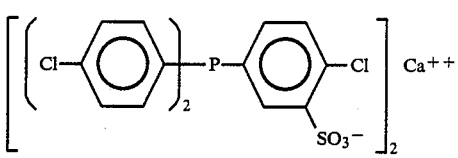
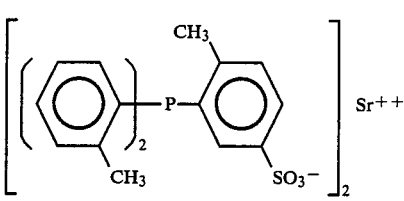
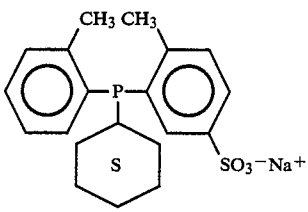
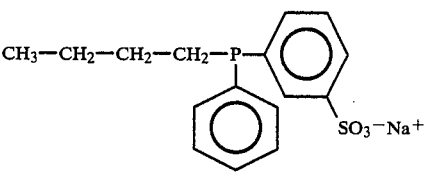
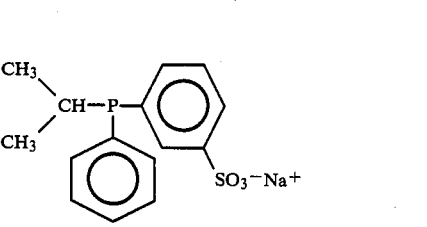

-continued

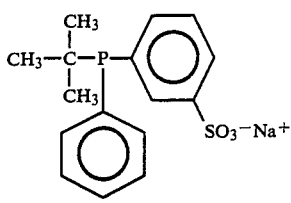

Such types of monosulfonated tertiary phosphine metal salts ligands employable in this invention and/or methods for their manufacture are well known, as seen e.g., by the procedures described in "J. Chem. Soc.", pp. 276–288 (1958) and U.S. Pat. No. 4,483,802. Preferably such ligands are prepared by sulfonating a corresponding phenyl containing tertiary phosphine, e.g.,

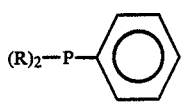

wherein R is the same as defined above with fuming sulfuric acid (oleum) under controlled temperature conditions to form predominately the corresponding protonated monosulfonated phenyl containing tertiary phosphine, e.g.,

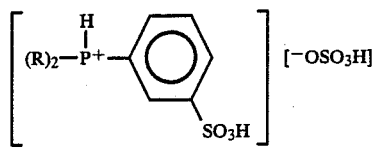

For instance, the solid phosphine is added to the fuming sulfuric acid in portions while controlling the temperature below 30° C. and then heated, e.g., to 70–80° C. until an aliquot from the reaction mixture does not show turbidity. The reaction mixture is then cooled immediately to stop any further sulfonation and without waiting added to water while controlling the temperature below 30° C. and said protonated phosphine salt then neutralized with a corresponding concentrated alkali or alkaline earth metal hydroxide to form the corresponding water-insoluble monosulfonated phenyl containing tertiary phosphine metal salt precipitate, e.g.,

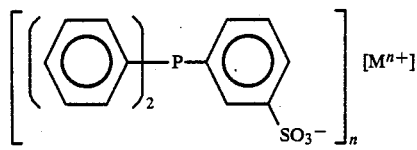

and by-product metal sulfate. The tertiary phosphine metal monosulfonate precipitate is then recovered after filtration by extracting it from the metal sulfate with methanol, followed by evaporation of the methanol. The crude tertiary phosphine metal monosulfonate precipitate may then be purified, if desired, by dissolving it in a suitable solvent such as water or ethanol and recrystallizing it therefrom. Of course it is understood that R, M and n in the above formulas are the same as already herein defined above.

Illustrative tertiary phosphines and metal hydroxides that may be used to prepare the monosulfonated tertiary phosphine metal salt ligands employable in this invention include for example, triphenylphosphine, diphenylcyclohexylphosphine, phenyldicyclohexylphosphine, diphenylisopropylphosphine, phenyldiisopropylphosphine, diphenyltertiary-butylphosphine, and the like; lithium hydroxide, sodium hydroxide, potassium hydroxide, cesium hydroxide, rubidium hydroxide, barium hydroxide, calcium hydroxide, strontium hydroxide, and the like. Moreover, if desired it may be possible to employ corresponding alkali or alkaline earth metal carbonates or bicarbonates as the neutralizing agent in place of the above mentioned hydroxide compounds.

It has now been surprisingly discovered that by the use of certain specialized added solubilizing agents, the monosulfonated tertiary phosphine metal salt ligands and Group VIII transition metal-monosulfonated tertiary phosphine metal salt ligand complex catalysts employable in this invention can be readily rendered organically soluble and thus employed in non-aqueous, hydroformylation reaction mediums, regardless of whether or not the hydroformylation process is directed to hydroformylating low molecular weight $C_2$–$C_5$ olefins or high molecular weight $C_6$ to $C_{20}$ olefins.

As noted above, such specialized added organic solubilizing agents include those selected from the group consisting of an alkylene oxide oligomer having an average molecular weight of at least 150, an organic nonionic surfactant mono-ol having an average molecular weight of at least 300, and a polar organic compound having a molecular weight of less than 150 and a Hildebrand solubility value of at least 10, as well as mixtures thereof.

While not intending to be bound by any precise explanation of exactly how such specialized solubilizing agents actually work in rendering such monosulfonated tertiary phosphine metal salt ligands and Group VIII transition metal-monosulfonated tertiary phosphine metal salt ligand complex catalysts soluble in the non-aqueous hydroformylation reaction medium, it is submitted that the solubilizing agents, which are themselves readily soluble in the non-aqueous hydroformylation reaction mediums, may be viewed as encapsulating the ligand salt and complex catalyst and thus rendering them soluble in the non-aqueous hydroformylation reaction mediums. Alternatively, the solubilizing agents may be viewed as coordinating with the ligand salt to form a complex which is soluble in the non-aqueous hydroformylation reaction medium thus also rendering the complex catalyst derived therefrom soluble in said reaction medium.

In any event, the subject invention is not predicated on knowing exactly how the added specialized solubilizing agent actually renders the generally insoluble ligand salts and catalysts soluble in the non-aqueous hydroformylation reaction mediums. Rather it is sufficient for the purpose of this invention to understand that when the hydroformylation reaction mediums also contain such an added specialized organic solubilizing agent, the ligand salts and complex catalysts derived therefrom are rendered soluble in said hydroformylation reaction mediums.

The alkylene oxide oligomers employable in this invention are liquids or low melting solids, which become liquid at the hydroformylation process reaction temperature, having an average molecular weight in the range of from about 150 to about 10,000, or higher, and include such oligomers as aliphatic polyalkylene oxide polyols and cyclic polyalkylene oxide ethers. Preferably such oligomers are those having an average molecular weight in the range of from 500 to about 7,000, and more preferably from 500 to about 2,000. Such compounds as well as methods for their preparation are well known. Such aliphatic polyalkylene oxide polyols include poly(oxyalkylene) glycols, polyalkylene oxide derivatives of glycerine (also commonly referred to as polyether triols), as well as polyether polyols having a functionality of greater than three, and the like. Such alcohols are readily available to the public e.g., under such trade names as CARBOWAX® PEG, CARBOWAX® TPEG, NIAX® PPG and UNCON® fluids (all products of Union carbide Corporation), as well as POLYGLYCOL-E® (Dow Chem. Co.) POLY-G® (Olin Corp.), PLURACOL-E® (BASF-Wyandotte Corp.), JEFFOX® (Texaco Inc.) and the like. Preferred poly(oxyalkylene) glycols include those represented by the following formula and mixtures thereof:

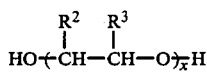

wherein x represents an integer, and $R^2$ and $R^3$ are selected from the qroup consisting of hydrogen and methyl radicals. Of course, each $R^2$ and $R^3$ group in a given compound may be the same or different. More preferably, the poly(oxyalkylene) glycols are selected from the group consisting of poly(oxyethylene) glycols, poly(oxypropylene) glycols, and mixtures thereof. Illustrative poly(oxyalkylene) glycols include CARBOWAX® PEG-600, a poly(oxyethylene) glycol having an average molecular weight of about 600, CARBOWAX® PEG-150, a poly(oxyethylene) glycol having an average molecular weight of about 150, NIAX® PPG-1025, a poly(oxypropylene) glycol havinq an average molecular weight of about 1025, and the like. Illustrative preferred polyalkylene oxide derivatives of glycerine include those represented by the following formula and mixtures thereof:

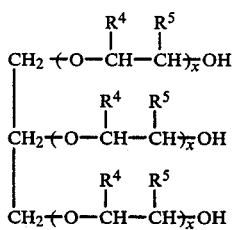

wherein x represents an integer, and $R^4$ and $R^5$ are selected from the group consisting of hydrogen and methyl radicals. Of course, each $R^4$ and $R^5$ group in a given compound may be the same or different. More preferably, the polyalkylene oxide derivatives of glycerine are polyethylene oxide derivatives of glycerine, such as CARBOWAX® TPEG-990, a polyethylene oxide derivative of glycerine having an averaqe molecular weight of about 990. Illustrative cyclic polyalkylene oxide ethers employable in this invention include the crown ethers described in U.S. Pat. No. 4,162,261. Crown ethers and/or methods for their manufacture are well known. Thus the crown ethers employable herein consist essentially of carbon, hydrogen and oxygen and may be termed monocyclic or polycyclic. Minor amounts of ether atoms which do not appreciably contribute to the solvency function of the crown ether according to this invention may also be present. In general, crown ethers contain in the principal ring at least 4 oxyqen atoms, each separated from the other by at least two aliphatic carbon atoms in series. Preferably, the principal ring contains at least two ring oxyqen atoms which are each joined to ethylene or substituted ethylene groups. The remainder of the principal ring oxygen atoms are joined to either trimethylene, tetramethylene, substituted trimethylene, or substituted tetramethylene groups, or mixtures thereof. Schematic characterizations of such crown ethers, as well as a more detailed description of such crown ethers can be found in said U.S. Pat. No. 4,162,261, the entire disclosure of which is encompassed herein by reference thereto. The preferred crown ethers do not contain more than 50 ether oxygen atoms in the principal ring and more preferably contain from 4 to 15 ether oxygen atoms in the principal ring. Moreover, because of their ease of manufacture monocyclic crown ethers are most preferred. Illustrative specific crown ethers include 15-crown-5 and 18-crown-6, and the like, such as shown and described in said U.S. Pat. No. 4,162,261.

The organic nonionic surfactant mono-ols employable in this invention are liquids having an average molecular weight in the range of from 300 to about 5000, or higher, the more preferred average molecular weight being in the range of from 500 to about 2000, and include such surfactants as alcohol alkoxylates. Such compounds as well as methods for their preparation are well known, as seen e.g., by U.S. Pat. No. 4,453,022 the entire disclosure of which is incorporated herein by reference thereto. Such alcohol alkoxylates are the reaction products of a monohydroxy alkyl compound or alkyl substituted phenol, wherein said alkyl radicals may contain from 4 to 25 carbon atoms, with an alkylene oxide. Of course it is to be understood that such monohydroxy alkyl compounds, in addition to individual mono-ols, may be mixtures of aliphatic mono-ols such as those derived by conventionally known methods from petroleum compounds or natural fats and oils. Illustrative alcohol alkoxylates include those represented by the following formula and mixtures thereof:

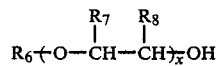

wherein x represents an integer, $R^6$ represents a radical selected from the group consisting of aliphatic primary, secondary and branched alkyl radicals, alkylphenyl radicals, and mixtures thereof, and $R^7$ and $R^8$ are selected from the group consisting of hydrogen and methyl radicals. Of course, each $R^7$ and group $R^8$ in a given alkoxylate may be the same or different. More preferably, each $R^7$ and $R^8$ roup represent hydrogen. the more preferred alcohol alkoxylates being alcohol ethoxylates.

The alcohol alkoxylates employable in this invention contain both water-soluble (polar) and oil-soluble (nonpolar) groups and are readily available to the public under such trade names as TERGITOLS® (Union Carbide Corporation), IGEPALS® (GAF Corp.), ALFONICS® (Conoco Inc.), BRIJ® (ICI), NEODOLS® (Shell Chem. Co.), STANDAMULS® (Henkel Corp.), SURFONICS® (Texaco Chem. Co.).

TRITONS ® (Rohm & Hass Co.), and the like, such as disclosed, for example in U.S. Pat. No. 4,453,022 and Kirk-Othmer's "Encyclopedia of Chemical Technology", Third Edition, Vol. 22, pp. 338-339 and 364-366 (1983). Among the more preferred alcohol alkoxylates are TERGITOLS ® such as those represented by the general alcohol ethoxylate formula $$R^6\text{-}(OCH_2CH_2)_x OH$$

wherein $R^6$ and x are the same as defined above as illustrated e.g. in the following TABLE.

TABLE

| Trade Name | $R^6$ | x |
| --- | --- | --- |
| TERGITOL ® 25-L-5 | $C_{12}$-$C_{15}$[a] | 5 |
| TERGITOL ® 26-L-5 | $C_{12}$-$C_{16}$[a] | 5 |
| TERGITOL ® 15-S-3 | $C_{11}$-$C_{15}$[b] | 3 |
| TERGITOL ® 15-S-7 | $C_{11}$-$C_{15}$[b] | 7 |
| TERGITOL ® NP-4 | nonylphenyl[c] | 4 |
| TERGITOL ® NP-9 | nonylphenyl[c] | 9 |
| TERGITOL ® 24-L-15N | $C_{12}$-$C_{14}$[a] | 4.8 |
| TERGITOL ® 24-L-50N | $C_{12}$-$C_{14}$[a] | 6.5 |
| TERGITOL ® 24-L-75N | $C_{12}$-$C_{14}$[a] | 8.0 |

[a]Linear - primary alkyls
[b]Linear - secondary alkyls
[c]Branched nonyl

The polar organic compounds that may also be employed as the added specialized organic solubilizing agent of this invention include organic liquids having a molecular weight of less than 150 and a Hildebrand solubility value of 10 or higher, and mixtures thereof. Illustrative examples of such polar compounds (along with their Hildebrand solubility parameters) include lower alcohols e.g., methanol (12.9), ethanol (11.2), propanol (10.2), isopropanol (10.2) and the like; as well as, nitriles e.g., benzonitrile (10.7), acetonitrile (11.8), propionitrile, and the like; N,N-disubstituted amides e.g., dimethylformamide (11.5), dimethylacetamide, N-methyl pyrolidone (14.8), and the like; sulfoxides e.g., dimethyl sulfoxide (12.8) and the like; sulfones e.g., dimethyl sulfone, sulfolane, and the like, and the like. Hildebrand solubility values are an empirical measure of the relative polarity of an organic compound and are described, e.g., in "Introduction to Modern Liquid Chromatography" by L. R. Snyder and J. J. Kirkland, pp. 215-218 (1974) a Wiley-Interscience publication, (John Wiley & Sons) and "The Solubility of Non-Electrolytes", J. H. Hildebrand and R. L. Scott, pp. 424-434, Dover Publications Inc., New York (1964).

As noted above there are three different compound classes of added specialized orqanic solubilizing agents, i.e., (a) alkylene oxide oligomers, (b) organic nonionic surfactant mono-ols and (c) organic polar compounds that may be employed in this invention. Moreover, as further noted, each compound class may be employed individually (i.e. one or more different solubilizing agents of the same compound class), or mixtures of two or more different compound classes (i.e. one or more different solubilizinq agents from the same compound class along with at least one or more different solubilizing agents from at least one or both of the other two different compound classes) may be employed in any given hydroformylation process of this invention. Of course, it is to be understood that regardless of whether or not such compound classes are employed individually or as mixtures, the total amount of added specialized organic solubilizing agent present in the non-aqueous hydroformylation reaction medium of a given process need only be that minimum amount necessary to render the monosulfonated tertiary phosphine metal salt ligand and complex catalyst derived therefrom that is employed, soluble in the non-aqueous hydroformylation reaction medium. In general, it is considered preferable to employ an excess of that minimum required, although no added benefit is seen in employing huge excess amounts. Accordingly when employed, either as an individual compound class or as part of a mixture of different compound classes, the alkylene oxide oligomer solubilizing agents of this invention may be employed in amounts ranging from about 1 to about 35 weight percent of the non-aqueous hydroformylation reaction medium (amounts ranging from about 1 to about 30 weight percent being preferred), the organic nonionic surfactant mono-ol solubilizing agents of this invention may be employed in amounts ranging from about 1 to about 60 weight percent of the non-aqueous hydroformylation reaction medium (amounts ranging from about 1 to about 50 weight percent being preferred), and the organic polar compound solubilizing agents of this invention may be employed in amounts ranging from about 1 to about 60 weight percent of the non-aqueous hydroformylation reaction medium (amounts ranging from about 1 to about 35 weight percent being preferred); with the proviso that, when a mixture of two or more different compound classes of such solubilizing agents is employed, the total amount of the sum of such solubilizing agents of said mixture employed is not greater than about 60 weight percent of the non-aqueous hydroformylation reaction medium, and preferably is not qreater than about 50 weight percent of the non-aqueous hydroformylation reaction medium. Of course, it is to be understood that the above maximum amount levels of the various three compound classes of solubilizing agents, as well as the above maximum amount level for a mixture of two or more different compound classes of such solubilizingg agents, pertains to the amount of solubilizing agent present in the hydroformylation reaction medium (i.e. reactor medium) of the process and not to that amount which might be present in a liquid recycle medium of a continuous process, said recycle medium having been concentrated, e.g. by removal and recovery of some of the desired aldehyde product. Likewise, it is to be understood that additional amounts of the specialized solubilizing agent may be added during the process, when and if desired, to maintain the desired amount level of solubilizing agent throughout the process, e.g. when additional ligand and/or catalyst is added to the process, provided that the above maximum amount levels of the various three individual compound classes of solubilizing agents and the above maximum amount level for any mixture of two or more different compound classes of such solubilizing agents are not exceeded. Further the manner and order of addition of the specialized solubilizing agent to the non-aqueous hydroformylation reaction medium is not critical, although it is generally preferred to employ same along with the metal salt ligand and complex catalyst right from the start of the process.

It has also been surprisingly discovered that certain monosulfonated tertiary phosphine metal salt ligands and their corresponding Group VIII transition metal-monosulfonated tertiary phosphine metal salt ligand complex catalysts may possess sufficient organic solubility in low molecular weight aldehydes (i.e., $C_3$ to $C_6$), so as to be able to be directly employable in such non-aqueous hydroformylation reactions directed to producing same without the need for any such additional specialized solubilizing agent. For instance it has been found that monosulfonated phosphine metal salts such as sodium, lithium and rubidium are quite soluble in such low molecular weight aldehydes and may be employed if desired to hydroformylate low molecular weight olefins (i.e. $C_2$ to $C_5$) in the absence of any such additional specialized solubilizing agents. Moreover, low concentrations (e.g. less than two weight percent) of monosulfonated cyclohexyl containing phosphine metal salt ligands may be useful in hydroformylating both low molecular weight ($C_2$ to $C_5$) and high molecular weight ($C_6$ to $C_{20}$) olefins in the absence of any such additional specialized solubilizing agents. However such instances appear to be the exception rather than the rule.

Accordingly another aspect of this invention can be described as an improved non-aqueous hydroformylation process for producing aldehydes which comprises reacting an alpha-olefin containing from 2 to 5 carbon atoms, with carbon monoxide and hydrogen, in a non-aqueous hydroformylation reaction medium containing the olefinically unsaturated organic compound, aldehyde product, solubilized Group VIII transition metal-phosphorus ligand complex catalyst and solubilized free phosphorus ligand, the improvement comprising employing as the phosphorus ligand of said complex catalyst and as said free phosphorus ligand, a monosulfonated tertiary phosphine metal salt the general formula

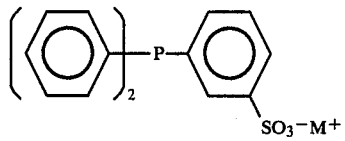

wherein M represents a metal cation selected from the group consisting of sodium, lithium and rubidium, wherein the organic solvent for said complex catalyst and said free ligand is selected from the group consisting of an aldehyde, a higher boiling aldehyde condensation by-product, and mixtures thereof, and wherein said hydroformylation process is carried out in the absence of any added organic solubilizing agent selected from the group consisting of an alkylene oxide oligomer having an average molecular weight of at least 150, an organic nonionic surfactant mono-ol having an average molecular weight of at least 300, a polar organic compound having a molecular weight of less than 150 and having a Hildebrand solubility value of at least 10, and mixtures thereof.

Still another aspect of this invention can be described as an improved non-aqueous hydroformylation process for producing aldehydes which comprises reacting an olefinically unsaturated organic compound with carbon monoxide and hydrogen, in a non-aqueous hydroformylation reaction medium containing the olefinically unsaturated organic compound, aldehyde product, solubilized Group VIII transition metal-phosphorus ligand complex catalyst and solubilized free phosphorus ligand, the improvement comprising employing as the phosphorus ligand of said complex catalyst and as said free phosphorus ligand, a monosulfonated tertiary phosphine metal salt the general formula

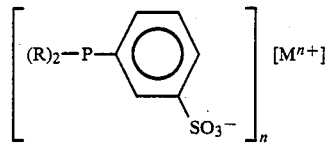

wherein one R group represents a cyclohexyl radical and the other R group represents a phenyl or cyclohexyl radical, wherein M represents a metal cation selected from the group consisting of alkali and alkaline earth metals, and wherein n has a value of 1 or 2 corresponding to the valence of the particular metal cation represented by M; wherein the organic solvent for said complex catalyst and said free ligand is selected from the group consisting of an aldehyde, a higher boiling aldehyde condensation by-product, and mixtures thereof, and wherein said hydroformylation process is carried out in the absence of any organics solubilizing agents selected from the group consisting of an alkylene oxide oligomer having an average molecular weight of at least 150 and organic nonionic surfactant mono-ol having an average molecular weight of at least 300 a polar organic compound having a molecular weight of less than 150 and having a Hildebrand solubility value of at least 10, and mixtures thereof.

It is to be noted that it has been surprisingly discovered that the molecular weight of the aldehyde product has a direct bearing on the solubilization of the monosulfonated tertiary phosphine metal salt ligands, and/or their corresponding Group VIII transition metal-monosulfonated tertiary phosphine metal salt complex catalysts, employable herein. Apparently the molecular weight determines the polarity of the aldehyde and in turn its solvency with said metal salt ligands and/or their corresponding complex catalysts. For instance, lower molecular weight aldehydes(e.g., $C_3$ to $C_6$) are more polar than high molecular weight aldehydes (e.g., $C_7$ to $C_{21}$). For example butyraldehyde is significantly more polar than nonanal, and thus allows for the solubilization of greater concentrations of e.g., a monosulfonated triphenylphosphine sodium salt ligand.

Accordingly while the alkylene oxide oligomers described above are useful as the added specialized solubilizing agent of this invention, when employing high salt concentrations, oligomer polyol-salt solutions tend to become very polar and may form a separate transparent liquid layer (i.e. a second organic phase) with non-polar aldehydes such as nonanal. Thus if one wishes to achieve and maintain a one-phase, homogeneous solution in such instances, one may include an additional specialized solubilizing agent or mixtures thereof selected from the group consisting of the organic nonionic surfactant mono-ols and the polar organic compounds, as described above, along with the alkylene oxide oligomer polyol involved.

Solutions of the monosulfonated tertiary phosphine metal salt ligands in the organic nonionic surfactant mono-ols employable in this invention, in qeneral, mix readily and totally even with non-polar aldehydes (e.g., nonanal) thus providing significantly higher monosulfonated tertiary phosphine metal salt solubilities than alkylene oxide oligomers. Further the nonionic surfactant mono-ols work synergistically with the alkylene oxide oligomers and when employed together can solubilize even higher metal salt ligand concentrations than can be achieved with either class of compounds used alone.

While the polar organic compound solubilizing agents mentioned above can also be readily employed to solubilize the monosulfonated tertiary phosphine metal salt ligands in both polar and non-polar aldehydes, one drawback in the utilization of such polar organic compounds, unlike the aforementioned alkylene oxide oligomers and/or nonionic surfactant mono-ols, is their high volatility. Such high volatility can cause stripping of the polar organic compound during catalyst-aldehyde product separation and may also cause ligand catalyst precipitation. Thus when used alone in a continuous operation the amount of polar organic compound employed may require careful monitoring and supplementation during the process. However, when used in conjunction with the non-volatile alkylene oxide oligomers and/or non-volatile nonionic surfactant mono-ols, said polar organic compounds can greatly enhance the metal salt ligand concentration solubility in mixtures of olefins and polar or non-polar aldehydes.

Of course it is to be further understood that the alkylene oxide oligomers and organic nonionic surfactant mono-ols employable in this invention and described above, comprise the condensation products of an alkylene oxide, such as e.g., ethylene oxide or propylene oxide, or mixtures of ethylene oxide and propylene oxide, with ethylene glycol (or glycerine) in the case of the alkylene oxide oligomers, or an alcohol in the case of the nonionic surfactant mono-ols, and that such conventional preparative procedures in general result in the production of a mixture of molecular weight condensation species containing a number of glycol, glycering or alcohol derivatives having different molecular proportions of alkylene oxide. Thus the product compounds obtained are, in reality, a mixture of derivatives of the glycol, glycerine or alcohol moiety containing different molecular portions of alkylene oxide units. Moreover in the case of alcohol alkoxylates, the alcohol moiety itself may be derived from one or more alcohols, e.g., a mixture of alcohols, such as $C_{11}$ to $C_{15}$ alkyl alcohols. Thus as is well known the conventional designation of the number of alkylene oxide units (x is the above alkylene oxide oligomer polyol and alcohol alkoxylate formulas) present in a molecule of alkylene oxide oligomer or alcohol alkoxylate, is a designation of the average number of alkylene oxide units per molecule and that a substantial proportion of the alkylene oxide oligomer or alcohol alkoxylate present is present as alkylene oxide oligomers or alcohol alkoxylates having a greater and a lesser number of alkylene oxide units present, than the average value, x, would indicate. Such designations of such products are well understood in the art and are employed herein consistent with their well understood meanings.

The Group VIII transition metals which make up the metal-monosulfonated tertiary phosphine salt ligand complexes of this invention include those selected from the group consisting of rhodium (Rh), cobalt (Co), iridium (Ir), ruthenium (Ru), iron (Fe), nickel (Ni), palladium (Pd), platinum (Pt) and osmium (Os), and mixtures thereof, with the preferred metals being Rh, Co, Ir and Ru, more preferably Rh and Co, especially Rh. It is to be noted that the successful practice of this invention does not depend and is not predicated on the exact structure of the catalytically active metal complex species, which may be present in their mononuclear, dinuclear and or higher nuclearity forms. Indeed the exact active structure is not known. Althouqh it is not intended herein to be bound to any theory or mechanistic discourse, it appears that the active catalytic species may in its simplest form consist essentially of the Group VIII transition metal in complex combination with the carbon monoxide and monosulfonated tertiary phosphine metal salt ligand.

The term "complex" as used herein and in the claims means a coordination compound formed by the union of one or more electronically rich molecules or atoms capable of independent existence with one or more electronically poor molecules or atoms, each of which is also capable of independent existence. As can be surmised from the above discussion, carbon monoxide (which is also properly classified as a ligand) is also present and complexed with the Group VIII transition metal. The ultimate composition of the active complex catalyst may also contain an additional organic ligand or anion satisfying the coordination sites or nuclear charge of the Group VIII transition metal as in the case of heretofore conventional Group VIII transition metal-triorganophosphine or phosphite catalysts such as e.g., hydrogen and the like. It is of course to be understood that the active complex species is preferably free of any additional organic ligand or anion that might poison the catalyst and have an undue adverse effect on catalyst performance. For instance it is known that in conventional rhodium catalyzed hydroformylation reactions that halogen anions can poison the catalyst. Accordingly it is preferred that in the rhodium catalyzed hydroformylation reactions of this invention that the active catalysts also be free of halogen directly bonded to the rhodium.

The number of available coordination sites on such Group VIII transition metals is well known in the art and may range in number from 4 to 6. By way of illustration it appears that the preferred active rhodium catalyst species of this invention contains, in its simplest form, an amount of monosulfonated tertiary phosphine metal salt ligand and carbon monoxide equal to a total of four moles in complex combination with one mole of rhodium. Thus the active species may comprise a complex catalyst mixture, in their monomeric, dimeric or higher nuclearity forms, which are characterized by one, two, and/or three monosulfonated tertiary phosphine metal salt molecules complexed per one molecule of rhodium. As noted above carbon monoxide is also present and complexed with the rhodium in the active species. Moreover, as in the case of conventional rhodium-triorganophosphine or phosphite ligand complexed catalyzed hydroformylation reactions wherein the active catalyst species is generally considered to also contain hydrogen directly bonded to the rhodium, it is likewise considered that the active species of the preferred rhodium catalyst employed in this invention during hydroformylation may also be complexed with hydrogen in addition to the monosulfonated tertiary phosphine metal salt and carbon monoxide ligands. Indeed it is believed that the active species of any Group VIII transition metal catalyst of this invention may also contain hydrogen in addition the monosulfonated tertiary phosphine metal salt and carbon monoxide ligands during hydroformylation, particularly in view of the hydrogen gas employed in the process.

Further, regardless of whether one preforms the active complex catalyst prior to introduction into the carbonylation reaction zone or whether the active species is prepared in situ during hydroformylation, the hydroformylation reaction is effected in the presence of free monosulfonated tertiary phosphine metal salt ligand. Thus by way of illustration the ultimate composition of the preferred active rhodium complex species catalyst can be likened or attributable to the outcome of competing reactions between carbon monoxide and the monosulfonated tertiary phosphine metal salt ligands for complexing or coordination sites with the rhodium element. These competing reactions can be disturbed or influenced, within significant limits, by increasing or decreasing the concentration of the monosulfonated tertiary phosphine metal salt ligand. As a eneralized statement, the component (carbon monoxide or monosulfonated tertiary phosphine metal salt ligand) which can shift the equilibrium of the competing reaction in its favor should enjoy the greater opportunities of occupying the coordination or complexing sites. For example, one may view the function of free monosulfonated tertiary metal phosphine salt ligand as either maintaining the status quo of the various forms of active complex catalyst during the hydroformylation, or as a means for shifting the equilibrium of the competing reactions in its favor and therefore causing additional monosulfonated tertiary phosphine metal salt ligands to enter into complex combination with rhodium with the probable eviction of a similar number of carbon monoxide ligands from the complex catalyst.

As noted above the monosulfonated tertiary phosphine metal salt ligands defined above are employed in this invention as both the phosphorus ligand of the Group VIII transition metal complex catalyst, as well as, the free phosphorus ligand that is present in the reaction medium of the process of this invention. In addition, it is to be understood that while the phosphorus ligand of the Group VIII transition metal-monosulfonated tertiary phosphine metal salt ligand complex catalyst and excess free monosulfonated tertiary phosphine metal salt ligand present in a given process of this invention are normally the same, different monosulfonated tertiary phosphine metal salt ligands, as well as, mixtures of two or more different monosulfonated tertiary phosphine metal salt ligands may be employed for each purpose in any given process, if desired.

As in the case of prior art Group VIII transition metal-phosphorus complex catalysts, the Group VIII transition metal-monosulfonated tertiary phosphine metal salt ligand complex catalysts of this invention may be formed by methods known in the art. For instance, preformed Group VIII transition metal hydrido carbonyl monosulfonated tertiary phosphine metal salt ligand complex catalysts may be prepared and introduced with an added specialized organic solubilizing agent as defined herein, if necessary, into the reaction medium of the hydroformylation process. More preferably, the Group VIII transition metal-monosulfonated tertiary phosphine metal salt ligand complex catalysts of this invention can be derived from a metal catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction medium along with the monosulfonated tertiary phosphine metal salt ligand and an added specialized organic solubilizing agent as defined herein, if necessary, for the in situ formation of the active catalyst. In a preferred embodiment rhodium dicarbonyl acetylacetonate is employed as a rhodium precursor and reacted in the presence of an added solubilizing agent as defined herein, if necessary, with the monosulfonated tertiary phosphine metal salt to form a catalytic rhodium carbonyl monosulfonated tertiary phosphine metal salt acetylacetonate precursor which is introduced into the reactor along with excess free monosulfonated tertiary phosphine metal salt ligand and an added specialized organic solubilizing agent as defined herein, if necessary, for the in situ formation of the active catalyst. In any event, it is sufficient for the purpose of this invention to understand that carbon monoxide, hydrogen and monosulfonated tertiary phosphine metal salt are all ligands that are capable of being complexed with the Group VIII transition metal, e.g., rhodium and that an active Group VIII transition metal-monosulfonated tertiary phosphine metal salt ligand complex catalyst is present in the reaction medium under the conditions of the hydroformylation process.

Moreover, like prior art Group VIII transition metal phosphorus ligand complex catalysts it is clear that the amount of complex catalyst present in the hydroformylation reaction medium of a given process of this invention need only be that minimum amount necessary to provide the given Group VIII transition metal concentration desired to be employed and which will furnish the basis for at least that catalytic amount of Group VIII transition metal necessary to catalyze the hydroformylation process. In general, Group VIII transition metal concentrations in the range of from about 10 ppm to about 1000 ppm, calculated as free metal, should be sufficient for most hydroformylation processes. Moreover, in the rhodium catalyzed hydroformylation processes of this invention, it is generally preferred to employ from about 10 to 800 ppm of rhodium calculated as free metal.

The olefinic starting material reactants encompassed by the processes of this invention can be terminally or internally unsaturated and be of straight-chain, branched-chain or cyclic structure. Such olefins can contain from 2 to 20 carbon atoms and may contain one or more ethylenic unsaturated groups. Moreover, such olefins may contain groups or substituents which do not essentially adversely interfere with the hydroformylation process such as carbonyl, carbonyloxy, oxy, hydroxy, oxycarbonyl, halogen, alkoxy, aryl, haloalkyl, and the like. Illustrative olefinic unsaturated compounds include alpha olefins, internal olefins, alkyl alkenoates, alkenyl alkenoates, alkenyl alkyl ethers, alkenols, and the like, e.g., ethylene, propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-octene, styrene, 3-phenyl- 1-propene, 1,4-hexadiene, 1,7-octadiene, 3-cyclohexyl-1-butene, allyl alcohol, hex-1-en-4-ol, oct-1-en-4-ol, vinyl acetate, allyl acetate, vinyl propionate, allyl propionate, allyl butyrate, methyl methacrylate, vinyl ethyl ether, vinyl methyl ether, allyl ethyl ether, n-propyl-7-octenoate, 3-butenenitrile, 5-hexenamide, and the like. Of course, it is understood that mixtures of different olefinic starting materials can be employed, if desired, by the hydroformylation process of the subject invention. The subject invention is especially useful for the production of aldehydes, by hydroformylating alpha olefins containing from 2 to 20 carbon atoms as well as starting material mixtures of such alpha olefins and internal olefins. The preferred olefin starting materials are low molecular weight alpha olefins having from 2 to 5 carbon atoms and more preferably high molecular weight alpha olefins containing from 6 to 20 carbon atoms, especially high molecular weight alpha olefins having from 6 to 14 carbon atoms. It is of course to be understood that commercial alpha olefins containing 4 or more carbon atoms may also contain minor amounts of corresponding internal olefins and/or their corresponding saturated hydrocarbon and that such commercial olefins need not necessarily be purified from same prior to being employed in this invention.

As noted above, the hydroformylation process of this invention is conducted by reacting an olefinically unsaturated organic compound with carbon monoxide and hydrogen in a non-aqueous hydroformylation reaction medium containing the olefinically unsaturated organic compound, aldehyde product, solubilized Group VIII transition metal-monosulfonated tertiary phosphine metal salt ligand complex catalyst and solubilized free monosulfonated tertiary metal salt ligand, the preferred organic solubilizing compound for the catalyst and free ligand being an added specialized organic solubilizing agent or mixtures thereof as herein defined above. Further as employed herein said non-aqueous hydroformylation reaction medium, be it in the form of one or more organic phases, is defined as the reaction medium in the reaction vessel (reactor) of the process and such reaction mediums may also contain higher boiling aldehyde liquid condensation by-products that are produced in situ, for example, during a continuous hydroformylation process. Indeed while such aldehyde condensation by-products may not be present in the reaction medium of a batch type process and need not be present at the start of a continuous process, the medium will in time normally eventually contain both aldehyde products and high boiling aldehyde liquid condensation by-products due to the nature of such continuous processes. For example, aldehyde condensation by-products also help serve as liquid carriers along with the aldehyde product for the solubilized catalyst and solubilized ligand in continuous liquid type catalyst recycle hydroformylation processes. Such aldehyde condensation by-products can also be preformed and used in any conventional manner if desired, e.g. as a diluent at the start-up of a process, and methods for their preparation are more fully described, e.g., in U.S. Pat. Nos. 4,148,830 and 4,247,486. It is to g further understood that if desired, organic diluents which do not unduly adversely interfere with the intended hydroformylation process of this invention may be employed and be present in the hydroformylation reaction medium, e.g. at the start-up of the process to help maintain the low concentration levels of the added specialized solubilizing agents in the hydroformylation reaction mediums. Preferred diluents include aldehydes and/or higher boiling aldehyde condensation by-products, corresponding to the aldehyde products and/or higher boiling aldehyde condensation by-products that may be produced by the intended hydrofromylation process, although any suitable different aldehyde and/or higher boiling aldehyde condensation type by-product may also be employed as such diluents. For example, Texanol ® (Eastman Chemical Products, Inc.), a 2,2,4-trimethyl-1,3-pentanediol monoisobutyrate trimer, is a convenient diluent for the production of butyraldehydes.

Further, as noted above, in certain instances, certain of the monosulfonated tertiary phosphine metal salt ligands and their corresponding Group VIII transition metal-monosulfonated tertiary phosphine metal salt ligand complex catalysts may possess sufficient organic solubility in such aldehydes and/or higher boiling aldehyde condensation by-products, so as to be directly employable in a non-aqueous hydroformylation process in the absence of any such added specialized solubilizing agents. In such instances, the aldehyde itself and/or its higher boiling aldehyde condensation by-product may serve as the organic solvent for the monosulfonated tertiary phosphine metal salt ligand and its corresponding complex catalyst. Finally, the amount of higher boiling aldehyde condensation by-product and/or organic diluent that might also be present in the hydroformylation reaction medium of this invention is mainly governed only by the amount of added specialized organic solubilizing agent for the catalyst and ligand that is also present and desired for the given hydroformylation reaction medium. Thus the non-aqueous hydroformylation reaction medium of this invention preferably consists essentially of the olefin starting material, aldehyde product, solubilized Group VIII transition metal-monosulfonated tertiary phosphine metal salt ligand complex catalyst, solubilized free monosulfonated tertiary phosphine metal salt ligand, added specialized organic solubilizing agent and optionally high boiling aldehyde condensation by-products, while in certain instances such non-aqueous hydroformylation reaction mediums may even be free of any such added specialized organic solubilizing agent.

It is further generally preferred to carry out the hydroformylation process of this invention in a continuous manner. Such types of continuous processes are well known in the art and may involve e.g., hydroformylating the olefinic starting material with carbon monoxide and hydrogen in a non-aqueous hydroformylation reaction medium containing the olefin, aldehyde product, the solubilized Group VIII transition metal-monosulfonated tertiary phosphine metal salt ligand complex catalyst, and solubilized free monosulfonated tertiary phosphine metal salt ligand and an added specialized organic solubilizing agent as defined herein, if necessary; supplying make-up quantities of the olefinic starting material, carbon monoxide and hydrogen to the reaction medium; maintaining reaction temperature and pressure conditions favorable to the hydroformylation of the olefinic starting material; and recovering the desired aldehyde hydroformylation product in any conventional manner desired. While the continuous process can be carried out in a single pass mode, i.e., wherein a vaporous mixture comprising unreacted olefinic starting material and vaporized aldehyde product is removed from the liquid reaction medium from whence the aldehyde product is recovered and make-up olefinic starting material, carbon monoxide and hydrogen are supplied to the liquid reaction medium for the next single pass through without recycling the unreacted olefinic starting material, it is generally desirable to employ a continuous process that involves either a liquid and/or gas recycle procedure. Of course it is to be understood that continuous processes involving solely a gas recycle procedure are not readily suitable for hydroformylating higher olefins of, e g., $C_6$ to $C_{20}$ carbon atoms, due to the low volatility of their aldehyde products. Such types of recycle procedures are well known in the art and may involve the liquid recycling of tne Group VIII transition metal-monosulfonated tertiary phosphine metal salt ligand complex catalyst solution separated from the desired aldehyde reaction product or a gas recycle procedure, or a combination of both a liquid and gas recycle procedure such as disclosed, e.g., in U.S. Pat. Nos. 4,148,830; 4,247,486 and 4,593,127, if desired. The most preferred hydroformylation process of this invention comprises a continuous liquid rhodium catalyst recycle process.

The desired aldehyde product may be recovered in any conventional manner such as described, e.g., in U.S. Pat. Nos. 4,148,830; 4,247,486 and 4,593,127. For instance, in a continuous liquid catalyst recycle process the portion of the liquid reaction solution (containing aldehyde product, catalyst, etc.) removed from the reactor can be passed to a vaporizer/separator wherein the desired aldehyde product can be separated via distillation, in one or more stags, under normal, reduced or elevated pressure, from the liquid reaction solution, condensed and collected in a product receiver, and further purified if desired. The remaining non-volatilized catalyst containing liquid reaction solution which also normally contains some of the aldehyde product and high boiling aldehyde condensation by-products, free phosphine liquid and specialized organic solubilizing agent may then be recycled back to the reactor, as may if desired, any other volatile materials. e.g., unreacted olefin, together with any hydrogn and carbon monoxide dissolved in the liquid reaction solution after separation thereof from the condensed aldehyde product, e.g., by distillation in any conventional manner. Alternatively the desired aldehyde products, in those cases where the non-aqueous hydroformylation reaction medium forms two organic liquid layers and causes separation of the catalyst components (rhodium, ligand and organic solubilizing agent) in the bottom layer and the aldehyde product and possibly some aldehyde condensation by-product and unreacted olefin in the top layer, may be recovered by simple separation of the two organic layers, e.g., by decantation of the aldehyde product layer, without the need to employ such distillation. At present, however, it is preferred to separate the desired aldehyde product from the rhodium catalyst containing product solution by vaporization under reduced pressure and at any suitable temperatures such as below 250° C. and more preferably below 200° C.

As noted above, the hydroformylation process of this invention is carried out in the presence of free monosulfonated tertiary phosphine metal salt ligand, i.e., ligand that is not complexed with the Group VIII transition metal of the metal complex catalyst employed and the free monosulfonated tertiary phosphine salt ligand may correspond to any of the above defined monosulfonated tertiary phosphine metal salt ligands discussed above. Thus the hydroformylation process of this invention may be carried out in any excess amount of free ligand desired, e.g., at least one mole of free monosulfonated tertiary phosphine metal salt ligand per mole of Group VIII transition metal present in the reaction medium. In gneral amounts of free ligand of from about 2 to about 300, and preferably from about 5 to about 200 moles per mole of Group VIII transition metal (e.g., rhodium) present in the reaction medium should be suitable for most purposes, particularly with regard to rhodium catalyzed hydroformylation. Of course, if desired, make-up monosulfonated tertiary phosphine metal salt ligand can be supplied to the reaction medium of the hydroformylation process, at any time and in any suitable manner, to maintain a predetermined level of free ligand in the reaction medium, if desired.

The reaction conditions for effecting the hydroformylation process of this invention may be those heretofore conventionally used and may comprise a reaction temperature of from about 45° C. to about 200° C. and pressures ranging from about 1 to 10,000 psia.

Of course, it is to be understood that while the optimization of the reaction conditions necessary to achieve the best results and efficiency desired are dependent upon one's experience in the utilization of the subject hydroformylation invention, only a certain measure of experimentation should be necessary to ascertain those conditions which are optimum for a given situation and such should be well within the knowledge of one skilled in the art and easily obtainable by following the more preferred aspects of this invention as explained herein and/or by simple routine experimentation.

For instance, the total gas pressure of hydrogen, carbon monoxide and olefinic unsaturated starting compound of the hydroformylation process of this invention may range from about 1 to about 10,000 psia. More preferably, however, in the hydroformylation of olefins to produce aldehydes it is preferred that the process be operated at a total gas pressure of hydrogen, carbon monoxide and olefinic unsaturated starting compound of less than about 1500 psia. and more preferably less than about 500 psia. The minimum total pressure of the reactants is not particularly critical and is limited predominately only by the amount of reactants necessary to obtain a desired rate of reaction. More specifically the carbon monoxide partial pressure of the hydroformylation process of this invention is preferably from about 1 to about 120 psia and more preferably from about 3 to about 90 psia, while the hydrogen partial pressure is preferably about 10 to about 160 psia and more preferably from about 20 to about 100 psia. In general $H_2:CO$ molar ratio of gaseous hydrogen to carbon monoxide may range from about 1:10 to 100:1 or higher, the more preferred hydrogen to carbon monoxide molar ratio being from about 1:1 to about 10:1.

Further as noted above the hydroformylation process of this invention may be conducted at a reaction temperature from about 45° C. to about 200° C. The preferred reaction temperature employed in a given process will of course be dependent upon the particular olefinic starting material and metal catalyst employed as well as the efficiency desired. In general, it is preferred to employ a reaction temperature of from about 60° C. to about 130° C. in rhodium-catalyzed hydroformulation processes.

Finally, the aldehyde products of the hydroformylation process of this invention have a wide range of utility that is well known and documented in the prior art e.g., they are especially useful as starting materials. for the production of alcohols and acids.

The beneficial factors involved in the employment of the monosulfonated tertiary phosphine metal salt ligands in this invention are many as described above, not the least of which is the wide processing latitude afforded one in selecting the proper combination of conditions that will be most useful in obtaining or at least best approaching a particular desired result or need. For instance the monosulfonated tertiary phosphine metal salt ligands can be used as the phosphorus ligand in non-aqueous rhodium catalyzed hydroformylation processes designed to produce aldehydes from both low as well as high molecular weight olefins at highly acceptable catalytic activity rates at even conventional preferred low hydroformylation pressures and/or low rhodium concentrations without unduly sacrificing processing efficiency and/or catalyst stability. Moreover the low volatility of the monosulfonated tertiary phosphine metal salt ligands of this invention (such salts are virtually non-volatile, i.e., they normally will decompose before they can be volatilized) render them especially suitable as a means for minimizing the undue ligand and/or catalyst loss that can be experienced during the aldehyde product separation (via distillation) of low volatile aldehydes derived from high molecular weight olefins (e.g., $C_6$ to $C_{20}$ carbon atoms) when conventional higher volatile phosphorus ligands are employed. Moreover the discovery of a suitable ligand, such as the monosulfonated tertiary phosphine metal salt ligands of this invention, which may be employed to provide a metal-phosphorus complex catalyst for the hydroformylation of both low molecular weight as well as high molecular weight, olefins clearly minimizes ligand and/or catalyst inventory storage problems and may possibly even do away with any need at all to switch ligands and/or catalyst, when one desires to change a commercial operation from one that has been producing low molecular weight aldehydes from low molecular weight olefins (e.g., $C_2$ to $C_5$ olefins) to one that is to produce high molecular weight aldehydes from high molecular weight olefins (e.g., $C_6$ to $C_{20}$ olefins). Further, the non-aqueous hydroformylation process of this invention to be readily retrofitted to existing non-aqueous hydroformylation design apparatus and equipment, without the need for major modifications of same. It has further been surprisingly observed that the normal (straight) chain to isomer (branched) chain aldehyde product ratio of the hydroformylation process of this invention may be varied and controlled over a wide range by simply varying the metal of the cation group of such ligands.

The following examples are illustrative of the present invention and are not to be regarded as limitative. It is to be understood that all of the parts, percentages and proportions referred to herein and in the appended claims are by weight unless otherwise indicated.

Texanol ® when employed in the following examples was used merely as a convenient diluent to demonstrate the efficacy of the low concentrations of the added specialized organic solubilizing agents in the hydroformylation reaction mediums and as a convenient medium for the reaction rate and isomer product ratio determinations in short term reactions. Texanol ® was also chosen as said diluent and medium because it is an isobutyaldehyde trimer and thus serves as a model for higher boiling aldehyde condensation by-products which are formed during a long term continuous recycle hydroformylation process. Surprisingly it was found that the Texanol ® could also be employed as an organic solvent for the monosulfonated triphenylphosphine lithium salts of Examples 1 and 3 and the monosulfonated cyclohexyl containing phosphine sodium salts of Examples 2 and 12.

EXAMPLE 1

A series of various rhodium complex catalyst precursor solutions consisting essentially of the solubilized reaction product of rhodium dicarbonyl acetylacetonate and various monosulfonated triphenylphosphine metal salt ligands were prepared and employed to hydroformylate propylene into $C_4$ aldehydes in the following manner.

Rhodium dicarbonyl acetylacetonate was mixed at ambient temperature with various triphenylphosphine monosulfonic acid metal salt ligands having the formula:

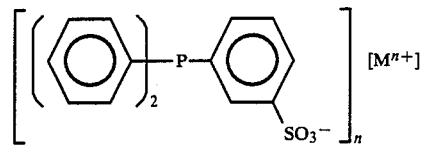

wherein M represents a metal as shown in TABLE 1 below, and wherein n represents an integer corresponding to the positive valance of the metal employed, and Texanol ® and varying amounts of Carbowax ® PEG-600 as the solubilizing agent to produce the various rhodium catalytic precursor solutions containing the amounts of rhodium and ligand shown in TABLE 1 below.

Each rhodium catalytic precursor solution so prepared was then employed to hydroformylate propylene in a magnetically stirred, 100 mL capacity, stainless steel autoclave which was attached to a gas manifold for introducing gases to the desired partial pressures. The autoclave was also equipped with a pressure calibrator for determining reaction pressure to ±0.01 psia. and a platinum resistance thermometer for determining reactor solution temperatures to ±0.10° C. The reactor was heated externally by two 300 watt heating bands. The reactor solution temperature was controlled by a platinum resistance sensor connected to an external proportional temperature controller for controlling the temperature of the external band heaters.

In each non-aqueous hydroformylation reaction, about 15 milliliters (about 14 grams) of the rhodium catalytic precursor solution so prepared was charged to the autoclave reactor under nitrogen and heated to the reaction temperature employed (as given in Table 1 below). The reactor was then vented down to 5 psig. and a premixed gas mixture of 1:1:1 carbon monoxide:-hydrogen:propylene was introduced into the reactor via the gas manifold (partial pressures given in Table 1) and the propylene so hydroformylated.

The hydroformylation reaction rate in gram moles per liter per hour of $C_4$ aldehydes produced was determined from sequential 5 psia. pressure drops in the reactor spanning the nominal operating pressure in the reactor, while the mole ratio of linear (n-butyraldehyde) to branched (2-methylpropionaldehyde) product was measured by gas chromatography and the results are given in Table 1 below.

TABLE 1

| Run No. | Ligand $M+=$ | Texanol ®/Carbowax ® PEG600 (Wt. Ratio) | Wt. % Carbowax ® PEG-600 | Reaction Rate Gmoles/L/Hr | Linear/Branched Aldehyde Mole Ratio |
|---|---|---|---|---|---|
| 1 | Li+ | 100:0$^d$ | 0 | 0.35$^a$ | 6.3 |
| 2 | Na+ | 10:1 | 8.5 | 0.28$^{b,c}$ | 6.4 |

TABLE 1-continued

| Run No. | Ligand M+= | Texanol ®/Carbowax ® PEG600 (Wt. Ratio) | Wt. % Carbowax ® PEG-600 | Reaction Rate Gmoles/L/Hr | Linear/Branched Aldehyde Mole Ratio |
|---|---|---|---|---|---|
| 3 | K+ | 9:1 | 8.7 | 0.87[a] | 5.1 |
| 4 | Rb+ | 8:1 | 10.0 | 0.70[a] | 5.6 |
| 5 | Cs+ | 7:1 | 10.85 | Declining Rate[a,e] | |
| 6 | Ca++ | 20:1 | 4.3 | 0.51[a] | 4.7 |
| 7 | Ba++ | 7:1 | 10.9 | 1.43[a] | 4.1 |
| 8 | Sr++ | 18:1 | 4.45 | No Rate[a,e] | — |

[a]Conditions: 200 ppm Rh; about 120 mole equivalents of ligand per mole of rhodium; 100° C.; 90 psia 1:1:1 $H_2$:CO:$C_3H_6$.
[b]Conditions: 200 ppm Rh; about 120 mole equivalents of ligand per mole of rhodium; 100° C.; 60 psia 1:1:1 $H_2$:CO:$C_3H_6$.
[c]Average of two runs.
[d]100% Texanol ®
[e]Results believed due to impure ligand.

EXAMPLE 2

The same procedure and conditions employed in Example 1 of preparing a rhodium catalytic precursor solution using rhodium dicarbonyl acetylacetonate, Texanol ®, and monosulfonated tertiary phosphine metal salt and hydroformylating propylene, was repeated employing the rhodium complex catalyst precursor solutions and hydroformylation reaction conditions as shown in Table 2 below. The monosulfonated tertiary phosphine metal salt ligand employed in Run No. 1 was a monosulfonated cyclohexyldiphenylphosphine sodium salt ligand (CHDPPMS-Na) having the formula

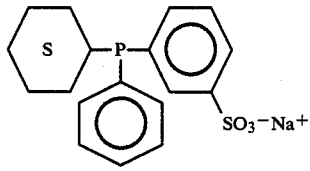

while the ligand used in Run No. 2 was a monosulfonated dicyclohexylphenylphosphine sodium salt ligand (DCHPPMS-Na) having the formula

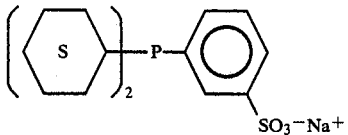

The hydroformylation reaction rate in terms of gram moles per liter per hour of $C_4$ aldehydes produced as well as the mole ratio of linear (n-butyraldehyde) to branched (2-methyl propionaldehyde) product were determined as in Example 1 and the results are given in Table 2 below.

TABLE 2

| Run No. | Ligand | Reaction Rate G moles/L/hr | Linear/Branched Aldehyde Mole Ratio |
|---|---|---|---|
| 1 | CHDPPMS-Na | 0.32 | 1.6 |
| 2 | DCHPPMS-Na | 0.78 | 1.2 |

Reaction Conditions: 100° C.; 240 ppm Rhodium; about 14 mole equivalents of ligand per mole of rhodium (0.9 wt. % ligand); 90 psia 1:1:1 $H_2$:CO:$C_3H_6$.

EXAMPLE 3

Continuous hydroformylation of butene-1 a monosulfonated triphenylphosphine metal salt ligand was conducted in the following manner.

The non-aqueous hydroformylation was conducted in a glass reactor operating in a continuous single pass butene-1 hydroformylation mode. The reactor consisted of a three-ounce pressure bottle submersed in an oil bath with a lass front for viewing. About 20-mL of a freshly prepared rhodium catalytic precursor solution was charged to the reactor with a syringe, after purging the system with nitrogen. The precursor solution contained about 200 ppm rhodium introduced as rhodium dicarbonyl acetylacetonate, about 118 mole equivalents of ligand per mole of rhodium of a monosulfonated triphenylphosphine lithium salt ligand of the formula

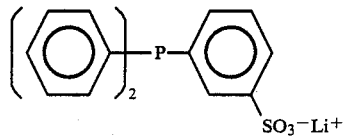

and Texanol ®. After closing the reactor, the system was again purged with nitrogen and the oil bath was heated to furnish the desired hydroformylation reaction temperature. The hydroformylation reaction was conducted at a total gas pressure of about 160 psig., the partial pressures of hydrogen, carbon monoxide, and butene-1 being given in Table 3 below, the remainder being nitrogen and aldehyde product.

The flows of the feed gases (carbon monoxide, hydrogen, butene-1 and nitrogen) were controlled individually with mass flow meters and the feed gases dispersed into the precursor solution via microporous stainless steel spargers. The reaction temperatures are given in Table 3 below. The unreacted portion of the feed gases was stripped out with the product $C_5$ aldehydes and the outlet gas analyzed over about 12 days of continuous operation. The approximate daily average reaction rates, in terms of gram moles per hour of product $C_5$ aldehydes, as well as the linear (n-valeraldehyde) to branched (2-methyl-butyraldehyde) product ratio are given in Table 3 below.

TABLE 3
TEST RESULTS - DAILY AVERAGES

| Days Opern | Temp °C. | Rhodium* ppm | Ligand* wt. % | Partial Pressures CO | Partial Pressures $H_2$ | Partial Pressures $C_4H_8$ | Rate gmoles/L/Hr | Linear/Branched Aldehyde Mole Ratio |
|---|---|---|---|---|---|---|---|---|
| 0.8 | 101. | 198. | 7.9 | 18. | 48. | 19 | 1.02 | 30.34 |
| 4.0 | 101. | 258. | 10.3 | 17. | 52. | 49 | 1.25 | 11.20 |
| 4.8 | 101. | 249. | 9.9 | 17. | 52. | 50 | 1.19 | — |
| 6.0 | 101. | 242. | 9.7 | 17. | 52 | 50 | 1.27 | 2.98 |
| 6.9 | 101. | 244. | 9.8 | 19. | 50. | 41 | 1.28 | 31.75 |
| 8.0 | 102. | 250. | 10.0 | 18. | 56. | 38 | 1.28 | 40.30 |
| 9.0 | 102. | 252. | 10.1 | 18. | 57. | 38 | 1.30 | 28.90 |
| 10.0 | 102. | 249. | 10.0 | 18. | 57. | 38 | 1.27 | 29.63 |
| 10.7 | 102. | 247. | 9.9 | 18. | 57. | 38 | 1.27 | 37.18 |
| 11.6 | 103. | 245. | 9.8 | 18. | 57. | 38 | 1.21 | 30.18 |

*Changing values reflect change in daily liquid reactor solution levels.

EXAMPLE 4

Butene-1 was continuously hydroformylated in the same manner as Example 3 using a catalyst precursor solution containing about 200 ppm rhodium introduced as rhodium dicarbonyl acetylacetonate, about a 10:1 (wt.:wt. ratio) mixture of Texanol ® and Carbowax ® PEG-600 (about 8.5 wt. %) as the solubilizing agent, and about 118 mole equivalents of ligand per mole of rhodium of a monosulfonated triphenylphosphine sodium salt ligand having the formula

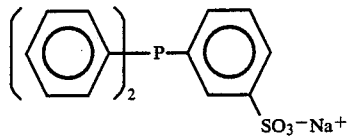

and the reaction conditions given in Table 4 below.

The approximate catalyst composition and daily average reaction rates, in terms of gram moles per liter per hour of product $C_5$ aldehydes, as well as the linear (n-valeraldehyde) to branched (2-methyl-butyraldehyde) product ratio are given in Table 4 below.

EXAMPLE 5

Butene-1 was continuously hydroformylated in the same manner as Example 3 using a catalyst precursor solution containing about 200 ppm rhodium introduced as rhodium dicarbonyl acetylacetonate, about a 20:1 (wt.:wt.ratio) mixture of Texanol ® and Carbowax ® PEG-600 (about 4.3 wt. %) as the solubilizing agent, and about 118 mole equivalents of ligand per mole of rhodium of a monosulfonated triphenylphosphine calcium salt ligand having the formula

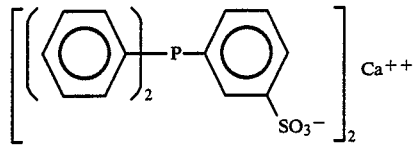

and the reaction conditions given in Table 5 below.

The approximate catalyst composition and daily average reaction rates, in terms of gram moles per liter per hour of product $C_5$ aldehydes, as well as the linear (n-valeraldehyde) to branched (2-methylbutyraldehyde) product ratio are given in Table 5 below.

TABLE 4
TEST RESULTS - DAILY AVERAGES

| Days Opern | Temp °C. | Rhodium* ppm | Ligand* wt. % | Partial Pressures (psia) CO | Partial Pressures (psia) $H_2$ | Partial Pressures (psia) $C_4H_8$ | Rate gmoles/L/Hr | Linear/Branched Aldehyde Mole Ratio |
|---|---|---|---|---|---|---|---|---|
| 0.9 | 102 | 197 | 5.9 | 51. | 59. | 20. | 1.68 | 7.68 |
| 2.0 | 101 | 206 | 6.2 | 51. | 47. | 22. | 1.81 | 9.21 |
| 3.0 | 101 | 220 | 6.6 | 20. | 53. | 24. | 1.60 | 21.08 |
| 4.0 | 101 | 226 | 6.8 | 20. | 30. | 39. | 2.50 | 19.83 |
| 5.9 | 101 | 224 | 6.7 | 15. | 63. | 31. | 2.06 | 22.82 |
| 5.6 | 101 | 223 | 6.7 | 15. | 64. | 31. | 2.05 | 23.74 |

*Changing values reflect change in daily liquid reactor solution levels.

TABLE 5
TEST RESULTS - DAILY AVERAGES

| Days Opern | Temp °C. | Rhodium* ppm | Ligand* wt. % | Partial Pressures (psia) CO | Partial Pressures (psia) $H_2$ | Partial Pressures (psia) $C_4H_8$ | Rate gmoles/L/Hr | Linear/Branched Aldehyde Mole Ratio |
|---|---|---|---|---|---|---|---|---|
| 0.9 | 101 | 179 | 3.9 | 20. | 59. | 20. | 1.27 | 12.84 |
| 1.7 | 101 | 178 | 3.9 | 19. | 55. | 18. | 1.38 | 14.44 |
| 5.0 | 101 | 213 | 4.7 | 16. | 47. | 36. | 1.62 | 13.06 |
| 5.9 | 101 | 222 | 4.9 | 17. | 51. | 29. | 1.64 | 17.67 |
| 7.0 | 101 | 220 | 4.8 | 13. | 43. | 50. | 1.85 | 20.95 |
| 8.0 | 101 | 235 | 5.2 | 17. | 41. | 36. | 2.09 | 18.76 |
| 9.0 | 102 | 245 | 5.4 | 17. | 36. | 52. | 2.19 | 18.38 |
| 10.0 | 102 | 261 | 5.7 | 18. | 30. | 56. | 1.40 | 20.52 |
| 11.9 | 102 | 287 | 6.3 | 17. | 29. | 59. | 1.62 | 21.86 |
| 11.8 | 102 | 317 | 7.0 | 17. | 29. | 63. | 1.51 | 18.90 |

TABLE 5-continued

TEST RESULTS - DAILY AVERAGES

| Days Opern | Temp °C. | Rhodium* ppm | Ligand* wt. % | Partial Pressures (psia) CO | H$_2$ | C$_4$H$_8$ | Rate gmoles/L/Hr | Linear/Branched Aldehyde Mole Ratio |
|---|---|---|---|---|---|---|---|---|
| 12.6 | 103 | 128 | 7.2 | 18. | 29. | .61. | 1.83 | 28.03 |

*Changing values reflect change in daily liquid reactor solution levels.

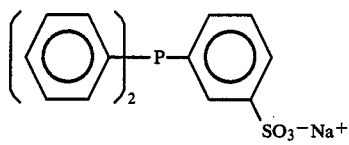

EXAMPLE 6

In a continuous catalyst liquid recycle manner, an olefin starting material of octene-1 was hydroformylated for six days as follows.

The liquid recycle reactor system employed contained two 2.8 liter stainless steel stirred tank reactors, connected in series, each containing a vertically mounted agitator and a circular tubular sparger near the bottom of the reactor for feeding the syn gas. The sparger contained a plurality of holes of sufficient size to provide the desired gas flow into the liquid body. Reactor 1 contained a silicone oil shell as means of bringing the contents of the reactors up to reaction temperature while the reaction solution in Reactor 2 was heated by an electrical heater. Both reactors contained internal cooling coils for controlling the reaction temperature. Reactors 1 and 2 were connected via a line to transfer any unreacted gases from reactor 1 to reactor 2 and were further connected via a line so that a portion of the liquid reaction solution containing aldehyde product and catalyst from reactor 1 could be pumped into reactor 2 wherein the unreacted olefin of reactor 1 is further hydroformylated in reactor 2.

Each reactor also contained a pneumatic liquid level controller for automatic control of the liquid levels in the reactors. Reactor 1 further contained a line for introducing the liquid olefin using a metering pump, and a line for introducing syn gas through the sparger, while make up syn gas was added to reactor 2 via the same transfer line carrying the unreacted syn gas from reactor 1. Reactor 2 also contained a blow-off vent for removal of the unreacted gases. A line from the bottom of reactor 2 was connected to the top of a vaporizer so that a portion of the liquid reaction solution could be pumped from reactor 2 to the vaporizer. The vaporizer was maintained at reduced pressure with the help of a vacuum pump. Vaporized aldehyde was disengaged from the non-volatilized components of the liquid reaction solution in the gas-liquid separator part of the vaporizer. The remaining non-volatilized catalyst containing liquid reaction solution was pumped through a recycle line back into reactor 1. The recycle line also contained a pneumatic liquid level controller. The vaporized aldehyde product was passed into a water-cooled condenser, liquified and collected in a product receiver.

The hydroformylation reaction was conducted by charging about 1.00 liters (893 grams) of a catalyst precursor solution of rhodium dicarbonyl acetylacetonate (about 600 ppm rhodium), about 16 wt. % of 3-(diphenylphosphino)-benzenesulfonic acid, sodium salt ligand having the formula (about 80 mole equivalents of ligand per mole of rhodium) and as the solubilizing agent, about 10 wt. % methanol, about 30 wt. % of a mixture 4:1 wt.:wt. ratio) of TERGITOL® 24-L-75N and CARBOWAX® TPEG 990, and about 45 wt. % of C$_9$ aldehyde, to reactor 1. About 1.00 liters (897 grams) of the same catalyst precursor solution was charged to reactor 2. The reactor system was then purged with nitrogen to remove any oxygen present, and the reactors heated to their reaction temperatures given in Table 6 below. Controlled flows of purified hydrogen and carbon monoxide were fed through the sparger into the bottom of reactor 1 and the reactor pressure increased to the operating pressure given in Table 6 below. When the liquid level in reactor 1 started to increase as a result of the pumping of liquid octane-1 and its conversion to liquid aldehyde product, a portion of the liquid reaction solution of reactor 1 was pumped into reactor 2 through a line into the top of reactor 2 at a rate sufficient to maintain a constant liquid level in reactor 1. The pressure of reactor 2 increased to its operating pressure given in Table 6 below. Blow-off gas from reactor 2 was analyzed and measured. A controlled flow of make-up syn gas (CO and H$_2$) was added to reactor 2 in order to maintain their desired partial pressures in reactor 2. The operating pressures and reaction temperatures were maintained throughout the hydroformylation. As the liquid level in reactor 2 started to increase as a result of the pumping from reactor and the liquid aldehyde product formation, a portion of the liquid reaction solution was pumped to the vaporizer/separator at a rate sufficient to maintain a constant liquid level in reactor 2. The crude aldehyde product was separated at 155° C. and about 40 mm Hg pressure from the liquid reaction solution, condensed and collected in a product receiver. The remaining non-volatilized catalyst containing liquid reaction solution was recycled back to reactor 1. The methanol present in the original catalyst composition was replenished by continuously adding methanol to reactor 1 using a Milton-Roy minipump. In the last two days of the test isopropanol alcohol was added in place of methanol. The methanol and to a lesser extent the isopropyl alcohol were partially reacting with the nonanal products forming the dimethyl and diisopropyl acetals respectively. These by-products were also continuously removed with the main reaction products by vaporization.

The hydroformylation of said octene-1 was carried out continuously for six days.

The hydroformylation reaction conditions as well as the rate of C$_9$ aldehydes produced in terms of gram moles per liter per hour and the linear to branched aldehyde product ratio of nonanal to 2-methyloctanal are given in Table 6 below.

TABLE 6

| | Days of Operation | | | |
|---|---|---|---|---|
| | 1 | 2 | 3 | 6 |
| Octene-1 feed, mole % | | | | |
| Octene-1 | 98.28 | 98.28 | 98.28 | 98.28 |
| Octene-2 | 1.54 | 1.54 | 1.54 | 1.54 |
| Octane | 0.17 | 0.17 | 0.17 | 0.17 |
| Reactor No. 1 | | | | |
| Temperature | 80.1 | 80.0 | 80.1 | 80.0 |
| Pressure, psia | 65.2 | 65.2 | 65.2 | 64.7 |
| H₂, psia | 47.6 | 56.9 | 56.6 | 50.7 |
| CO, psia | 17.0, | 7.8 | 8.1 | 10.1 |
| Octene-1 mole % | 24.4 | 22.3 | 22.8 | 20.2 |
| Octene-2 mole % | 5.2 | 5.4 | 5.4 | 4.6 |
| Reactor No. 2 | | | | |
| Temperature | 85.8 | 85.6 | 85.7 | 85.0 |
| Pressure, psia | 51.7 | 50.7 | 51.7 | 50.7 |
| H₂, psia | 40.1 | 48.1 | 44.7 | 39.7 |
| CO, psia | 9.9 | 2.2 | 6.5 | 8.3 |
| Octene-1 mole % | 10.8 | 8.6 | 7.0 | 5.3 |
| Octene-2 mole % | 5.4 | 7.2 | 6.2 | 5.6 |
| Results | | | | |
| C₉ Aldehydes/ gmoles/L/hr | 1.02 | 0.84 | 0.81 | 1.02 |
| Linear/Branched Aldehyde Ratio | 14.0 | 27.2 | 24.7 | 22.5 |

Daily analysis via High Performance Liquid Chromatography of the hydroformylation reaction mediums in both reactors showed no significant change in the ligand concentration of said mediums over the six days of operation.

EXAMPLE 7

Butene-1 was continuously hydroformylated in the same manner as Example 3 using a catalyst precursor solution containing about 200 ppm rhodium introduced as rhodium dicarbonyl acetylacetonate, about a 7:1 (wt. :wt.ratio) mixture of Texanol® and Carbowax® PEG-600 (about 10.9 wt. %) as the solubilizing agent, and about 118 mole equivalents of ligand per mole of rhodium of a monosulfonated triphenylphosphine barium salt ligand having the formula

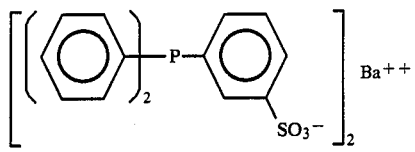

and the reaction conditions given in Table 7 below.

The approximate catalyst composition and daily average reaction rates, in terms of gram moles per liter per hour of product C₅ aldehydes, as well as the linear (n-valeraldehyde) to branched (2-methylbutyraldehyde) and product ratio are given in Table 7 below.

TABLE 7

| Days Opern | Temp °C. | Rhodium* ppm | Ligand* wt. % | Partial Pressures (psia) | | | Rate gmoles/L/Hr | Linear/Branched Aldehyde Mole Ratio |
|---|---|---|---|---|---|---|---|---|
| | | | | CO | H₂ | C₄H₈ | | |
| 1.0 | 101. | 186. | 5.1 | 18. | 70. | 11. | 2.07 | 6.91 |
| 1.8 | 101. | 183. | 5.0 | 16. | 62. | 14. | 2.10 | 7.10 |
| 5.0 | 101. | 183. | 5.0 | 12. | 66. | 19. | 2.51 | 7.12 |
| 5.9 | 101. | 203. | 5.6 | 13. | 66. | 20. | 2.52 | 7.03 |
| 6.9 | 101. | 195. | 5.4 | 14. | 62. | 22. | 2.71 | 6.32 |
| 7.9 | 101. | 187. | 5.1 | 16. | 55. | 24. | 2.71 | 6.16 |
| 9.0 | 102. | 200. | 5.5 | 18. | 60. | 23. | 2.73 | 6.01 |
| 7.0 | 102. | 207. | 5.7 | 18. | 62. | 22. | 2.60 | 6.02 |
| 11.0 | 102. | 220. | 6.1 | 19. | 63. | 21. | 2.46 | 6.20 |
| 11.7 | 102. | 234. | 6.4 | 20. | 63. | 21. | 2.37 | 6.14 |
| 12.6 | 103. | 240. | 6.6 | 20. | 63. | 22. | 2.30 | 5.85 |

*Changing values reflect change in daily liquid reactor solution levels.

EXAMPLE 8

Propylene was continuously hydroformylated in the same manner as Example 3 using a catalyst precursor solution containing about 200 ppm rhodium introduced as rhodium dicarbonyl acetylacetonate, about an 8:1 (wt.:wt.ratio) mixture of Texanol* and Carbowax*-PEG-600 (about 10.0 wt. %) as the solubilizing agent, and about 118 mole equivalents of ligand per mole of rhodium of a monosulfonated triphenylphosphine rubidium salt ligand having the formula

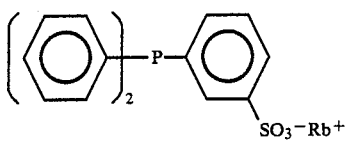

and the reaction conditions given in Table 8 below.

The approximate catalyst composition and daily average reaction rates, in terms of gram moles per liter per hour of product C₄ aldehydes, as well as the linear (n-butyraldehyde) to branched (2-methylpropionaldehyde) product ratio are given in Table 8 below.

TABLE 8

| Days Opern | Temp °C. | Rhodium* ppm | Ligand* wt. % | Partial Pressures (psia) | | | Rate gmoles/L/Hr | Linear/Branched Aldehyde Mole Ratio |
|---|---|---|---|---|---|---|---|---|
| | | | | CO | H₂ | C₃H₆ | | |
| 1.0 | 99. | 244. | 7.3 | 33. | 53. | 17. | 1.01 | 5.15 |
| 2.0 | 106. | 272. | 8.2 | 28. | 54. | 18. | 1.24 | 6.19 |
| 3.0 | 102. | 182. | 5.5 | 23. | 55. | 19. | 0.68 | 5.86 |
| 4.0 | 102. | 189. | 5.7 | 23. | 55. | 19. | 0.58 | 6.04 |
| 4.9 | 104. | 202. | 6.1 | 23. | 55. | 19. | 0.58 | 6.12 |
| 5.8 | 103. | 216. | 6.5 | 23 | 55. | 20. | 0.58 | 6.45 |

TABLE 8-continued

| Days Opern | Temp °C. | Rhodium* ppm | Ligand* wt. % | Partial Pressures (psia) CO | H₂ | C₃H₆ | Rate gmoles/L/Hr | Linear/Branched Aldehyde Mole Ratio |
|---|---|---|---|---|---|---|---|---|
| 6.7 | 98. | 222. | 6.7 | 24. | 56. | 20. | 0.41 | 6.60 |

*Changing values reflect change in daily liquid reactor solution levels.

EXAMPLE 9

The solubilities of various monosulfonated triphenylphosphine metal salt ligands having the formula

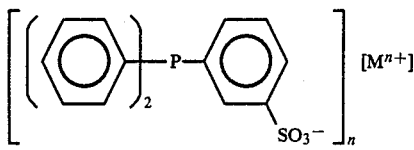

wherein M represents a metal as shown in Table 9 below and n represents an integer corresponding to the positive valance of the metal employed, were measured in different aldehydes by adding incremental amounts of the various solid metal salt ligands into the various well-stirred aldehydes maintained at a constant temperature until a saturated solution was obtained. The results of such tests are reported in Table 9 below.

TABLE 9

| Aldehyde | Temp. °C. | Metal Salt Solubility (Wt. %) Wherein M Represents | | | |
|---|---|---|---|---|---|
| | | Li⁺ | Na⁺ | Rb⁺ | Ba⁺⁺ |
| Propionaldehyde | 35 | 8.8 | 16.3 | 6.6 | 0.5 |
| Butyraldehyde | 60 | 0.5 | 10.0 | 1.4 | 0.6 |
| Valeraldehyde | 80 | <0.5 | 5.3 | 3.3 | 0.1 |
| Heptanal | 80 | <0.7 | 0.4 | 3.8 | 0.2 |
| Nonanal | 80 | <0.5 | 0.5 | 0.9 | 0.2 |
| Tridecanal | 80 | <0.5 | 0.5 | 0.5 | 0.3 |

EXAMPLE 10

The solubility of various monosulfonated triphenylphosphine metal salt ligands having the formula

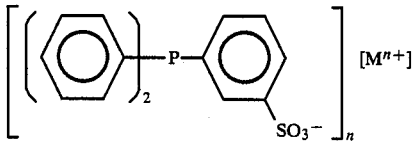

wherein M represents a metal as shown in Table 10 below an n represents an integer corresponding to the positive valance of the metal employed, were measured in nonanal in the presence of an added solubilizing agent consisting of 1.5 grams of a (1:4 wt.:wt.ratio) mixture of CARBOWAX® TPEG-900 and TERGITOL® NP-9, for the ligands. The solubilization was determined by measuring the solubility of varying amounts of the salt ligands in said solubilizing agent mixture at 100° C., then three grams of nonanal and observing whether a homogeneous solution was maintained at ambient temperature. The calculated weight percent solubilities for the various ligands are reported in Table 10 below.

TABLE 10

| Metal Salt M = | Wt. % Solubility 25° C. |
|---|---|
| Li⁺ | 12 |
| Na⁺ | 25 |
| Rb⁺ | 25 |
| Cs⁺ | >10 |
| Ca⁺⁺ | 18 |
| Ba⁺⁺ | 33 |

EXAMPLE 11

The same procedure and conditions employed in Example 1 of preparing various rhodium catalytic precursor solutions using rhodium dicarbonyl acetylacetonate, a monosulfonated triphenylphosphine sodium salt ligand having the formula

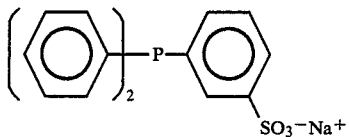

and about a 3.5:1 (wt.:wt. ratio) mixture of Texanol® and about 20 wt. % of an added solubilizing agent or mixture of solubilizing agents as given in Table 11 (which also gives the weight ratios of said mixtures of solubilizing agents) below for said ligand and hydroformylating propylene was repeated employing the various rhodium complex catalyst precursor solutions and hydroformylation reaction conditions as shown in Table 11 below. The hydroformylation reaction rate in terms of gram moles per liter per hour of C₄ aldehydes produced as well as the mole ratio of linear (n-butyraldehyde) to branched (2-methyl propionaldehyde) product were determined as in Example 1 and the results are given in Table 11 below.

TABLE 11

| Run No. | Added Solubilizing Agent | Reaction Rate G moles/ L/hr | Linear/ Branched Aldehyde Mole Ratio |
|---|---|---|---|
| 1 | TERGITOL ®NP-9 | 0.67 | 5.1 |
| 2 | TERGITOL ®15-S-7 | 0.49 | 4.7 |
| 3 | TERGITOL ®24-L-75N/NIAX ® PPG 1025 (4:1) | 0.54 | 5.3 |
| 4 | TERGITOL ®NP-4/ CARBOWAX ® TPEG 990 (4:1) | 0.59 | 6.0 |
| 5 | TERGITOL ®15-S-3/ CARBOWAX ® PEG 600/ Dimethyl Sulfoxide (4:1:1) | 0.25 | 5.6 |
| 6 | TERGITOL ®15-S-7/ CARBOWAX ® TPEG 990/ N—Methyl Pyrolidone (4:1:1) | 0.75 | 5.0 |

Reaction Conditions: 100° C.; 200 ppm Rhodium; about 120 mole equivalents of ligand per mole of rhodium (8.3 wt. % Ligand); 90 psia 1:1:1 H₂:CO:C₃H₆.

EXAMPLE 12

Butene-1 was continuously hydroformylated in the same manner as Example 3 using a catalyst precursor solution containing about 200 ppm rhodium introduced as rhodium dicarbonyl acetylacetonate, Texanol ® and about 14 mole equivalents of ligand per mole of rhodium of a monosulfonated dicyclohexyl phenylphospine sodium salt ligand having the formula

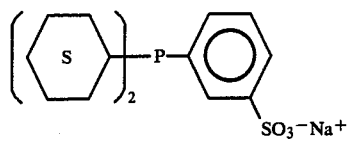

and the reaction conditions given in Table 12 below.

The approximate catalyst composition and daily average reaction rates, in terms of gram moles per liter per hour of product $C_5$ aldehydes, as well as the linear (n-valeraldehyde) to branched (2-methylbutyraldehyde) product ratio are given in Table 1 below.

TABLE 12
TEST RESULTS -- DAILY AVERAGES

| Days Opern | Temp °C. | Rhodium* ppm | Ligand* wt. % | Partial Pressures (psia) CO | $H_2$ | $C_4H_8$ | Rate gmoles/ L/Hr | Linear/ Branched Aldehyde Mole Ratio |
|---|---|---|---|---|---|---|---|---|
| 0.8 | 80 | 172 | 0.8 | 40 | 39 | 3 | 0.86 | 1.86 |
| 1.9 | 80 | 168 | 0.8 | 38 | 41 | 4 | 1.02 | 1.88 |
| 2.8 | 80 | 182 | 0.8 | 39 | 41 | 3 | 0.87 | 1.99 |
| 3.9 | 80 | 186 | 0.8 | 38 | 42 | 4 | 0.85 | 1.84 |
| 5.0 | 80 | 191 | 0.9 | 38 | 42 | 4 | 0.88 | 1.83 |
| 5.8 | 80 | 195 | 0.9 | 38 | 42 | 5 | 0.86 | 1.79 |
| 6.8 | 80 | 200 | 0.9 | 38 | 43 | 4 | 0.80 | 1.95 |
| 7.8 | 80 | 249 | 1.1 | 38 | 44 | 5 | 0.86 | 1.78 |
| 9.0 | 80 | 257 | 1.2 | 39 | 43 | 5 | 0.72 | 1.75 |
| 10.0 | 80 | 272 | 1.2 | 42 | 38 | 6 | 0.94 | 1.79 |
| 10.9 | 80 | 274 | 1.2 | 41 | 39 | 6 | 0.95 | 1.89 |
| 11.0 | 80 | 274 | 1.2 | 41 | 39 | 6 | 0.99 | 1.92 |
| 12.9 | 80 | 299 | 1.3 | 41 | 39 | 5 | 0.95 | 1.77 |

*Changing values reflect change in daily liquid reactor solution levels.

EXAMPLE 13

The same procedure and conditions employed in Example 1 of preparing a rhodium catalytic precursor solution using rhodium dicarbonyl acetylacetonate, about a 9:1 (wt.:wt.ratio) mixture of TEXANOL ® and CARBOWAX ® TPEG-990 (about 10.0 wt. %) as the solubilizing agent, and monosulfonated triphenylphosphine sodium salt ligand having the formula

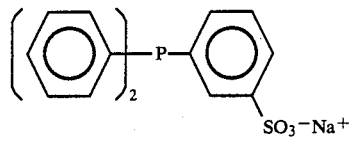

and hydroformylating dodecene-1 was repeated employing the various rhodium complex catalyst precursor solutions and various hydroformylation reaction conditions as shown in Table 13 below. The hydroformylation reaction rate in terms of gram moles per liter per hour of $C_{13}$ aldehydes produced as well as the mole ratio of linear (n-tridecanal) to branched (2-methyl dodecanal) product were determined as in Example 1 and the results are given in Table 13 below.

TABLE 13

| Run No. | Rh* ppm | Temp °C. | Ligand/ Rhodium Mole Ratio | Partial $H_2$ psia | Pressures CO psia | Olefin Dodecene-1 ml | Reaction Rate Gram/Moles L/Hr | Linear/ Branched Aldehyde Mole Ratio |
|---|---|---|---|---|---|---|---|---|
| 1 | 25 | 100 | 10 | 20 | 40 | 5.0 | 1.37 | 3.4 |
| 2 | 200 | 120 | 200 | 20 | 40 | 5.0 | 1.24 | 9.56 |
| 3 | 500 | 70 | 50 | 20 | 40 | 5.0 | 0.51 | 5.5 |
| 4 | 200 | 100 | 100 | 10 | 40 | 5.0 | 1.13 | 16.9 |
| 5 | 200 | 100 | 100 | 100 | 40 | 5.0 | 1.41 | 4.1 |

Rh* = Rhodium

EXAMPLE 14

The same procedure and conditions employed in Example 1 of preparing various rhodium catalytic precursor solutions using rhodium dicarbonyl acetylacetonate, about a 3:1 (wt.:wt. ratio) mixture of Texanol ® and CARBOWAX ® TPEG-990 (about 25 wt. %) as the solubilizing agent, and a monosulfonated triphenylphosphine sodium salt ligand having the formula

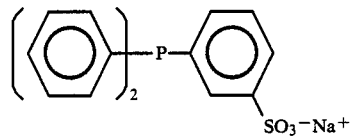

and hydroformylating an olefin was repeated employing the various rhodium complex catalyst precursor solutions and using different alpha olefins as the hydroformylation feedstocks and the reaction conditions as shown in Table 14 below. The hydroformylation reaction rates in terms of gram moles per liter per hour of aldehydes produced as well as the mole ratio of linear aldehyde to branched aldehyde product were determined as in Example 1 and the results are given in Table 14 below.

TABLE 14

| Run No. | Alpha-Olefin | Reaction Rate G moles/L/hr | Linear/ Branched Aldehyde Mole Ratio |
|---|---|---|---|
| 1 | Propylene[a] | 1.72 | 5.0 |
| 2 | Butene-1[b] | 5.96 | 12.8 |
| 3 | Hexene-1[b] | 5.21 | 13.4 |
| 4 | Octene-1[b] | 4.17 | 14.8 |
| 5 | Dodecene-1[b] | 1.04 | 10.8 |
| 6 | Tetradecene-1[b] | 0.65 | 12.6 |

[a]Reaction Conditions: 90° C.; 300 ppm Rhodium; 8.7 wt. % Ligand; Ligand:Rhodium mole ratio = 80:1; 90 psia 1:1:1 $H_2$:CO:$C_3H_6$.
[b]Reaction Conditions: 100° C.; 300 ppm Rhodium; 8.7 wt. % Ligand; Ligand:Rhodium mole ratio = 80:1; 30 m moles olefin; 75 psia 4:1 $H_2$:CO.

EXAMPLE 15

The same procedure and conditions employed in Example 1 of preparing various rhodium catalytic precursor solutions using rhodium dicarbonyl acethylacetonate, a monosulfonated triphenylphosphine sodium salt ligand having the formula

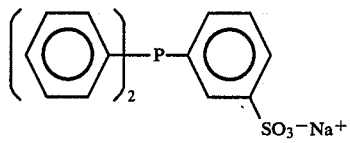

and various mixtures of Texanol ® and varying amounts (about 15 wt. % in Run No. 1 and about 10 wt. % in Run Nos. 2 to 5) of different added solubilizing agents as given in Table 15 below, and hydroformylating octene-1 was repeated employing the various rhodium complex catalyst precursor solutions and the reaction conditions as shown in Table 15 below. The hydroformylation reaction rate in terms of gram moles per liter per hour of $C_9$ aldehydes produced as well as the mole ratio of linear (n-nonanal) to branched 2-methyl octylaldehyde) product were determined as in Example 1 and the results are given in Table 15 below.

TABLE 15

| Run No. | TEXANOL ®/ Solubilizing Agent (wt.:wt. Ratio) | Reaction Rate G moles/L/hr | Linear/ Branched Aldehyde Mole Ratio |
|---|---|---|---|
| 1 | Texanol ®/Dimethyl Sulfoxide (5.5:1) | 0.95 | 18.7 |
| 2 | Texanol ®/Benzo-Nitrile (8:1) | 0.47 | 26.6 |
| 3 | Texanol ®/Sulfolane (8:1) | 0.98 | 19.1 |
| 4 | Texanol ®/Carbo-wax ® PEG 150 | 1.12 | 17.6 |
| 5 | Texanol ®/Niax ® PPG-1025 | 0.71 | 23.9 |

Reaction Conditions: 90° C.; 200 ppm Rhodium; 10 wt. % Ligand; Ligand:Rhodium mole ratio = 137; 5 mL Octene-1; 75 psia 4:1 $H_2$:CO.

EXAMPLE 16

The solubility of a monosulfonated triphenylphosphine sodium salt ligand (TPPMS-Na) having the formula

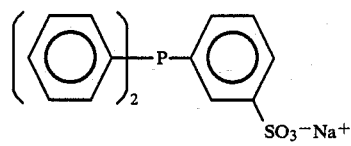

was measured in $C_9$ aldehyde (nonanal) in the presence of various added solubilizing agents and various mixtures of such agents for the ligand. The solubility measurements were carried out by dissolving the solid TPPMS-Na ligand in the solubilizing agent or mixtures thereof at 100° C., then adding the nonanal and observing whether or not a homogeneous solution was maintained at both 100° C. and ambient temperature. The solubilizing agents and their mixtures were employed in a 1:2 weight:weight ratio with the nonanal. The results are reported in Table 16 below:

TABLE 16

| | Weight Percent TPPMS-Na Solubility | |
|---|---|---|
| Solubilizing Agent | 25 deg. C. | 100 deg. C. |
| TERGITOL ® NP-4 | 2 | 6 |
| TERGITOL ® NP-9 | 4 | 6 |
| TERGITOL ® 15-S-3 | 2 | 8 |
| TERGITOL ® 15-S-7 | 4 | 8 |
| TERGITOL ® 24-L-15N | 2 | 8 |
| TERGITOL ® 24-L-50N | 4 | 8 |
| TERGITOL ® 24-L-75N | 6 | 8 |
| TERGITOL ® 25-L-5 | 4 | 6 |
| TERGITOL ® 26-L-5 | 2 | 6 |
| CARBOWAX ® PEG-600 | >8a | >8a |
| CARBOWAX ® TPEG-990 | >2a | >2a |
| NIAX ® PPG-1025 | <2 | 2 |
| Binary Systems (Wt. Ratio) | | |
| TERGITOL ® NP-4/CARBOWAX ® TPEG 990(4:1) | 8 | 10 |
| TERGITOL ® 15-S-7/CARBOWAX ® TPEG 990 (3:1) | 10 | 8 |
| TERGITOL ® 24-L-75N/CARBOWAX ® TPEG 990 (4:1) | 12 | 14 |
| TERGITOL ® NP-9/CARBOWAX ® PEG 600 (3:1) | 10 | >10 |
| TERGITOL ® 15-S-3/CARBOWAX ® PEG 600 (4:1) | 2 | >10 |
| TERGITOL ® 24-L-50N/CARBOWAX ® PEG 600 (4:1) | >10 | >10 |
| TERGITOL ® 24-L-75N/NIAX ® PPG 1025 (2:1) | >10 | >10 |
| Ternary Systems (Wt. Ratio) | | |

TABLE 16-continued

| | Weight Percent TPPMS-Na Solubility | |
|---|---|---|
| | 25 deg. C. | 100 deg. C. |
| TERGITOL ® 24-L-75N/CARBOWAX ® TPEG 990/Methanol (4:1:1) | >16 | — |
| TERGITOL ® 15-S-3/CARBOWAX ® PEG 600/Methanol (4:1:1) | >6 | — |
| TERGITOL ® NP-9/CARBOWAX ® PEG 600/Methanol (3:1:1) | >12 | — |

[a]Two translucent layers are formed.

EXAMPLE 17

The solubility of a monosulfonated triphenylphosphine sodium salt ligand (TPPMS-Na) having the formula

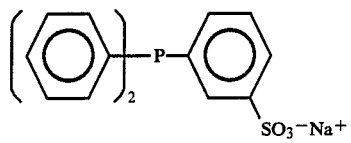

was determined in various aldehydes by dissolving the solid TPPMS-Na ligand in a solubilizing agent mixture of TERGITOL® 24-L-75N/CARBOWAX® TPEG-900 (4:1 wt.:wt. ratio) at 100° C., then adding the aldehyde and observing whether or not a homogeneous solution was maintained at ambient temperature. The solubilizing agent mixture was employed in a 1:2 weight:weight ratio with the various aldehydes. The results are given in Table 17 below:

TABLE 17

| Aldehyde | Weight Percent TPPMS-Na Solubility at 25 deg. C. |
|---|---|
| Butyraldehyde | >20 |
| Valeraldehyde | >20 |
| Heptanal | 18 |
| Nonanal | 12 |

TABLE 17-continued

| Aldehyde | Weight Percent TPPMS-Na Solubility at 25 deg. C. |
|---|---|
| Tridecanal | 8 |

EXAMPLE 18

The same procedure and conditions employed in Example 1 of preparing a rhodium catalytic precursor solution using rhodium dicarbonyl acetylacetonate, various monosulfonated triphenylphosphine metal salt ligands as shown in Table 18 below, and about a 3.5:1 (wt.:wt. ratio) mixture of heptanal and about 20 weight percent of an added solubilizing agent or mixture of solubilizing agents as given in Table 18 below (which also gives the weight ratios of said mixtures of solubilizing agents) for the ligand employed, and hydroformylating dodecene-1 was repeated employing the various rhodium complex catalyst precursor solutions and hydroformylation reaction conditions as shown in Table 18 below. The hydroformylation reaction rate in terms of gram moles per liter per hour of aldehydes produced as well as the mole ratio of linear (n-tridecanal) to branched (2-methyl dodecanal) product were determined as in Example 1 and the results are given in Table 18 below.

TABLE 18

| Run No. | Phosphine Ligand | Added Solubilizing Agent[e] | Reaction Rate G moles/L/hr | Linear/Branched Aldehyde Mole Ratio |
|---|---|---|---|---|
| 1. | TPPMS-Na[a] | TERGITOL ® NP-9 | 0.77 | 14.2 |
| 2. | " | CARBOWAX ® PEG-600 | 0.72 | 12.0 |
| 3. | " | TERGITOL ® 24-L-75N/CARBOWAX ® TPEG-990 (4:1) | 0.62 | 13.6 |
| 4. | " | TERGITOL ® 15-S-3/NIAX ® PPG-1025/Dimethyl Sulfoxide (4:1:1) | 0.51 | 13.2 |
| 5. | TPPMS-Ba[b] | CARBOWAX ® PEG-600 | 1.22 | 10.0 |
| 6. | " | TERGITOL ® 24-L-75N/CARBOWAX ® TPEG-990 (4:1) | 0.76 | 10.9 |
| 7. | " | TERGITOL ® 15-S-7/Carbowax ® TPEG-990 (3:1) | 0.45 | 9.4 |
| 8. | TPPMS-Rb[c] | CARBOWAX ® PEG-600 | 0.69 | 16.3 |
| 9. | TPPMS-Li[d] | CARBOWAX ® PEG-600 | 0.30 | 13.7 |

Reaction Conditions: 100° C.; 200 ppm Rhodium; about 120 mole equivalents of ligand per mole of rhodium; 60 psia 2:1 $H_2:CO$; 5 mL (3.7 g) dodecene-1
[a]TPPMS-Na = 8.3 wt. % of a monosulfonated triphenylphosphine sodium salt having the formula as shown in Example 4.
[b]TPPMS-Ba = 9.3 wt. % of a monosulfonated triphenylphosphine barium salt having the formula as shown in Example 7.
[c]TPPMS-Rb = 9.7 wt. % of a monosulfonated triphenylphosphine rubidium salt having the formula as shown in Example 8.
[d]TPPMS-Li = 7.9 wt. % of a monosulfonated triphenylphosphine lithium salt having the formula as shown in Example 3.
[e]In Run Nos. 2, 5, 6, 8 and 9, two liquid organic phase layers were observed in the hydroformylation reaction medium; the top layer being colorless and clear and the bottom layer being yellow. Such, however, had no adverse affect on the hydroformylation reaction.

EXAMPLE 19

A comparison of the catalytic activity of aqueous and non-aqueous solutions of monosulfonated triphenylphosphine sodium salt ligand promoted catalysts in hydroformylating various molecular weight alphe-olefins was determined as follows.

The same procedure and conditions employed in Example 1 of preparing rhodium catalytic precursor solutions, using rhodium dicarbonyl acetylacetonate, monosulfonated triphenylphosphine sodium salt having the formula as shown in Example 4 in either a non-aqueous organic solubilizing agent solution or water, as given in Table 19 below, and hydroformylating the various alpha-olefins was repeated employing the various rhodium complex precursor solutions and hydroformylation reaction conditions as shown in Table 19 below. Both the aqueous and non-aqueous hydroformylation reactions were conducted under identical conditions with regard to temperature, rhodium and ligand concentration, hydrogen and carbon monoxide partial pressure and olefin concentration. The hydroformylation reaction rates in terms of gram moles per liter per hour of aldehydes produced as well as the mole ratio of linear to branched aldehyde product were determined as in Example 1 and the results are given in Table 19 below.

TABLE 19

| | Non-Aqueous Hydroformylation Reaction Medium | | Aqueous Hydroformylation Reaction Medium | |
|---|---|---|---|---|
| Olefin | Reaction Rate G Moles/L/Hr | Linear/Branched Aldehyde Mole Ratio | Reaction Rate G Moles/L/Hr | Linear/Branched Aldehyde Mole Ratio |
| Propylene | 2.60$^a$ | 4.8 | 0.07$^c$ | 19.3 |
| Butene-1 | 6.94$^b$ | 5.1 | 0.44$^d$ | 37.1 |
| Octene-1 | 2.84$^b$ | 5.8 | 0.11$^d$ | 40.9 |
| Dodecene-1 | 4.49$^b$ | 6.6 | 0.03$^d$ | 43.4 |

$^a$Reaction Conditions: 300 ppm Rhodium; 8.7 wt. % Ligand (80:1 moles of ligand per mole of rhodium); 2.6:1 (wt.:wt. ratio) of a mixture of Texanol ® and Carbowax ® TPEG-990 (about 25 wt. %) as the solubilizing agent; 100° C.; 90 psia 1:1:1 H$_2$:CO:Propylene.
$^b$Reaction Conditions: 300 ppm Rhodium; 8.7 wt. % Ligand (80:1 moles of ligand per mole of rhodium); 2.6:1 (wt.:wt. ratio) of a mixture of Texanol ® and Carbowax ® TPEG-990 (about 25 wt. %) as the solubilizing agent; 100° C.; 90 psia 1:1 H$_2$:CO; 5 mL of the respective olefin.
$^c$Reaction Conditions: 300 ppm Rhodium; 8.7 wt. % Ligand (80:1 moles of ligand per mole of rhodium); water as the solvent; 100° C.; 90 psia 1:1:1 H$_2$:CO:Propylene.
$^d$Reaction Conditions: 300 ppm Rhodium; 8.7 wt. % Ligand (80:1 moles of ligand per mole of rhodium); water as the solvent; 100° C.; 90 psia 1:1 H$_2$:CO; 5 mL of the respective olefin.

Various modifications and variations of this invention will be obvious to a worker skilled in the art and it is to be understood that such modifications and variations are to be included within the purview of this application and the spirit and scope of the appended claims.

What is claimed is:

1. In a non-aqueous hydroformylation process for producing aldehydes which comprises reacting an olefinically unsaturated organic compound containing from 2 to 20 carbon atoms with carbon monoxide and hydrogen, in a non-aqueous hydroformylation reaction medium containing the olefinically unsaturated organic compound, aldehyde product, solubilized rhodium-phosphorus ligand complex catalyst and solubilized free phosphorus ligand, and wherein the hydroformylation reaction conditions comprise a reaction temperature of from about 45° C. to about 200° C., a total gas pressure of hydrogen, carbon monoxide and olefinically unsaturated compound of less than about 500 psia, a carbon monoxide partial pressure of from about 1 to 120 psia, a hydrogen partial pressure of from about 10 to 160 psia and wherein said reaction medium contains at least about 2 moles of total free phosphorus ligand per mole of rhodium in said medium, the improvement comprising employing as the phosphorus ligand of said complex catalyst and as said free phosphorus ligand, a monosulfonated tertiary phosphine metal salt the general formula

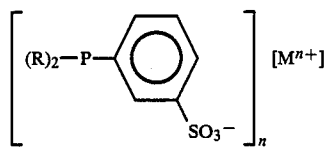

wherein each R group individually represents a radical containing from 1 to 30 carbon atoms selected from the class consisting of alkyl, aryl, alkaryl, aralkyl and cycloakyl radicals; wherein M represents a metal cation selected from the group consisting of alkali and alkaline earth metals, and wherein n has a value of 1 or 2 corresponding to the valence of the particular metal cation represented by M; and wherein said hydroformylation reaction medium also contains at least a sufficient amount of an added organic solubilizing agent capable of rendering the rhodium-monosulfonated tertiary phosphine metal salt ligand complex catalyst and free monosulfonated tertiary phosphine metal salt ligand employed, soluble in said hydroformylation reaction medium; and wherein said organic solubilizing agent is selected from the group consisting of an alkylene oxide oligomer having an average molecular weight of at least 150, an organic nonionic surfactant mon-ol having an average molecular weight of at least 300, a polar organic compound having a molecular weight of less than 150 and having a Hildebrand solubility value of at least 10, and mixtures thereof; provided that when present in the hydroformylation reaction medium, the amount of said alkylene oxide oligomer is not greater than about 35 weight percent of said medium, the amount of said organic nonionic surfactant mono-ol is not greater than about 60 weight percent of said medium, and the amount of said polar organic compound is not greater than about 60 weight percent of said medium, with the additional proviso that the total amount of added organic solubilizing agent present in said medium is not greater than about 60 weight percent of said medium.

2. A process as defined in claim 1, wherein higher boiling aldehyde condensation by-products are also present in the non-aqueous hydroformylation reaction medium, wherein the partial pressure of carbon monoxide is from about 3 to about 90 psia and wherein the partial pressure of hydrogen is from about 20 to about 100 psia.

3. A process as defined in claim 2, wherein the olefinically unsaturated compound is an alpha olefin containing from 2 to 5 carbon atoms, and wherein each R group individually represents a radical selected from the group consisting of a branched alkyl radical having from 3 to 9 carbon atoms, phenyl and cyclohexyl radicals and wherein the reaction temperature is from about 60° C. to about 130° C.

4. A process as defined in claim 3, wherein each R group individually represents a phenyl or cyclohexyl radical.

5. A process as defined in claim 4, wherein the alpha olefin is propylene or butene-1.

6. A process as defined in claim 4, wherein M+ represents an alkali metal selected from the group consisting of lithium, sodium, potassium, cesium and rubidium and wherein n is 1.

7. A process as defined in claim 4, wherein M+ represents an alkaline earth metal selected from the group consisting of calcium, barium, magnesium and strontium and n is 2.

8. A process as defined in claim 6 wherein M+ is sodium and each R group represents a phenyl radical.

9. A process as defined in claim 7 wherein M+ is sodium and each R group represents a cyclohexyl radical.

10. A process as defined in claim 6, wherein M+ is sodium and one R group represents a phenyl radical while the other R group represents a cyclohexyl radical.

11. A process as defined in claim 3, wherein when present in the hydroformylation reaction medium, the amount of said alkylene oxide oligomer is not greater than about 30 weight percent of said medium, the amount of said nonionic surfactant mono-ol is not greater than about 50 weight percent of said medium, and the amount of said polar organic compound is not greater than about 35 weight percent of said medium; with the additional proviso that the total amount of added organic solubilizing agent present in said medium is not greater than about 50 weight percent of said medium.

12. A process as defined in claim 4, wherein the added organic solubilizing agent is an alkylene oxide oligomer.

13. A process as defined in claim 12, wherein the alkylene oxide oligomer is selected from the group consisting of a poly(oxethylene) glycol, a poly(oxypropylene) glycol and a polyethylene oxide derivative of glycerine, and mixtures thereof.

14. A process as defined in claim 4, wherein the added organic solubilizing agent is an organic nonionic surfactant mono-ol.

15. A process as defined in claim 14, wherein the organic nonionic surfactant mono-ol represents an alcohol alkoxylate.

16. A process as defined in claim 15, wherein the alcohol alkoxylate is an alcohol ethoxylate.

17. A process as defined in claim 4, wherein the added organic solubilizing agent is a polar organic compound.

18. A process as defined in claim 17, wherein the polar organic compound is selected from the group consisting of methanol, ispropanol, dimethyl sulfoxide, N-methyl pyrrollidone, benzonitrile and sulfolane.

19. A process as defined in claim 4 wherein the added organic solubilizing agent is a mixture of an alkylene oxide oligomer and an organic nonionic surfactant mono-ol.

20. A process as defined in claim 4, wherein the added organic solubilizing agent is a mixture of an alkylene oxide oligomer and a polar organic compound.

21. A process as defined in claim 4, wherein the added organic solubilizing agent is a mixture of an organic nonionic surfactant mono-ol and a polar organic compound.

22. A process as defined in claim 4, wherein the added organic solubilizing agent is a mixture of an alkylene oxide oligomer, an organic nonionic surfactant mono-ol and a polar organic compound.

23. A process as defined in claim 2, wherein the olefinically unsaturated compound is an alpha olefin containing from 6 to 20 carbon atoms.

24. A process as defined in claim 23, wherein the alpha olefin contains from 6 to 14 carbon atoms, and wherein each R group individually represents a radical selected from the group consisting of a branched alkyl radical having from 3 to 9 carbon atoms, phenyl and cyclohexyl radicals and wherein the reaction temperature is from about 60° C. to about 130° C. and wherein the total gas pressure of hydrogen, carbon monoxide and olifinically unsaturated compound is about 140 psia or less.

25. A process as defined in claim 24, wherein each R group individually represents a phenyl or cyclohexyl radical.

26. A process as defined in claim 25, wherein M+ represents an alkali metal selected from the group consisting of lithium, sodium, potassium, cesium and rubidium and wherein n is 1.

27. A process as defined in claim 25, wherein M+ represents an alkaline earth metal selected from the group consisting of calcium, barium, magnesium and strontium and n is 2.

28. A process as defined in claim 26, wherein M+ is sodium and each R group represents a phenyl radical.

29. A process as defined in claim 26, wherein M+ is sodium and each R group represents a cyclohexyl radical.

30. A process as defined in claim 26, wherein M+ is sodum and one R group represents a phenyl radical while the other R group represents a cyclohexyl radical.

31. A process as defined in claim 23, wherein when present in the hydroformylation reaction medium, the amount of said alkylene oxide oligomer is not greater than about 30 weight percent of said medium, the amount of said nonionic surfactant mono-ol is not greater than about 50 weight percent of said medium, and the amount of said polar organic compound is not greater than about 35 weight percent of said medium; with the additional proviso that the total amount of added organic solubilizing agent present in said medium is not greater than about 50 weight percent of said medium.

32. A process as defined in claim 25, wherein the added organic solubilizing agent is an alkylene oxide oligomer.

33. A process as defined in claim 32, wherein the alkylene oxide oligomer is selected from the group consisting of a poly(oxyethylene) glycol, a poly(oxypropylene) glycol and a polyethylene oxide derivative of glycerine, and mixtures thereof.

34. A process as defined in claim 25, wherein the added organic solubilizing agent is an organic nonionic surfactant mono-ol.

35. A process as defined in claim 34, wherein the organic nonionic surfactant mono-ol represents an alcohol alkoxylate.

36. A process as defined in claim 35, wherein the alcohol alkoxylate is an alcohol ethoxylate.

37. A process as defined in claim 25, wherein the added organic solubilizing agent is a polar organic compound.

38. A process as defined in claim 37, wherein the polar organic compound is selected from the group consisting of methanol, isopropanol, dimethyl sulfoxide, N-methyl pyrrolidone, benzonitrile and sulfolane.

39. A process as defined in claim 25, wherein the added organic solubilizing agent is a mixture of an alkylene oxide oligomer and an organic nonionic surfactant mono-ol.

40. a process as defined in claim 25, wherein the added organic solubilizing agent is a mixture of an alkylene oxide oligomer and a polar organic compound.

41. A process as defined in claim 25, wherein the added organic solubilizing agent is a mixture of an organic nonionic surfactant mono-ol and a polar organic compound.

42. A process as defined in claim 25, wherein the added organic solubilizing agent is a mixture of an alkylene oxide oligomer, and organic nonionic surfactant mono-ol and a polar organic compound.

43. A process as defined in claim 23, wherein the hydroformylation process comprises a continuous catalyst containing liguid recycle procedure.

44. In a non-aqueous hydroformylation process for producing aldehydes which comprises reacting an alpha-olefin containing from 2 to 5 carbon atoms, with carbon monoxide and hydrogen, in a non-aqueous hydroformylation reaction medium containing the olefinically unsaturated organic compound, aldehyde product, solubilized rhodium-phosphorus ligand complex catalyst and solubilized free phosphorus ligand, and wherein the hydroformylation reaction conditions comprise a reaction temperature of from about 45° C. to about 200° C., a total gas pressure of hydrogen, carbon monoxide and olefinically unsaturated compound of less than about 500 psia; a carbon monoxide partial pressure of from about 1 to 120 psia, a hydrogen partial pressure of about 10 to 160 psia and wherein said reaction medium contains at least about 2 moles of total free phosphorus ligand per mole of rhodium in said medium, the improvement comprising employing as the phosphorus ligand of said complex catalyst and as said free phosphorus ligand, a monosulfonated tertiary phosphine metal salt the general formula

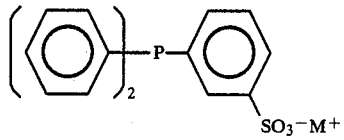

wherein M represents a metal cation selected from the group consisting of sodium, lithium and rubidium, wherein the organic solvent for said complex catalyst and said free ligand is selected from the group consisting of an aldehyde, a higher boiling aldehyde condensation by-product, and mixtures thereof, and wherein said hydroformylation process is carried out in the absence of any added organic solubilizing agent selected from the group consisting of an alkylene oxide oligomer having an average molecular weight of at least 150, an organic nonionic surfactant mono-ol having an average molecular weight of at least 300, a polar organic compound having a molecular weight of less than 150 and having a Hildebrand solubility value of at least 10, and mixtures thereof.

45. In a non-aqueous hydroformylation process for producing aldehydes which comprises reacting an olefinically unsaturated organic compound containing from 2 to 20 carbon atoms with carbon monoxide and hydrogen, in a non-aqueous hydroformylation reaction medium containing the olefinically unsaturated organic compound, aldehyde product, solubilized rhodium-phosphorus ligand complex catalyst and solubilized free phosphorus ligand, and wherein the hydroformylation reaction conditions comprise a reaction temperature of from about 45° C. to about 200° C., a total gas pressure of hydrogen, carbon monoxide and olefinically unsaturated compound of less than about 500 psia; a carbon monoxide partial pressure of from about 1 to 120 psia, a hydrogen partial pressure of about 10 to 160 psia and wherein said reaction medium contains at least about 2 moles of total free phosphorus ligand per mole of rhodium in said medium, the improvement comprising enploying as the phosphorus ligand of said complex catalyst and as said free phosphorus ligand, a monosulfonated tertiary phosphine metal salt the general formula

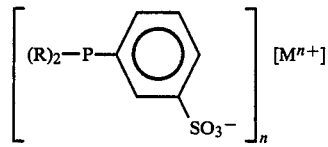

wherein one R group represents a cyclohexyl radical and the other R group represents a phenyl or cyclohexyl radical wherein M represents a metal cation selected from the group consisting of alkali and alkaline earth metals, and wherein n has a value of 1 to 2 corresponding to the valence of the particular metal cation represented by M; wherein the organic solvent for said complex catalyst and said free ligand is selected from the group consisting of an aldehyde, a higher boiling aldehyde condensation by-product, and mixtures thereof, and wherein said hydroformylation process is carried out in the absence of any organic solubilizing agent selected from the group consisting of an alkylene oxide oligomer having an average molecular weight of at least 150, an organic nonionic surfactant mono-ol having an average molecular weight of at least 300, a polar organic compound having a molecular weight of less than 150 and having a Hildebrand solubility value of at least 10, and mixtures thereof.

* * * * *